(12) United States Patent
Reed et al.

(10) Patent No.: US 8,207,152 B2
(45) Date of Patent: *Jun. 26, 2012

(54) METHODS FOR TREATING OR PREVENTING CANCER BY PREVENTING, INHIBITING, OR ARRESTING CELL CYCLING

(75) Inventors: Michael John Reed, Slough (GB); Barry Victor Lloyd Potter, Slough (GB)

(73) Assignee: Sterix Limited, Berskshire (GB)

(*) Notice: Subject to any disclaimer, the term of this patent is extended or adjusted under 35 U.S.C. 154(b) by 440 days.

This patent is subject to a terminal disclaimer.

(21) Appl. No.: 11/244,416

(22) Filed: Oct. 5, 2005

(65) Prior Publication Data

US 2006/0122161 A1 Jun. 8, 2006

Related U.S. Application Data

(62) Division of application No. 09/561,453, filed on Apr. 28, 2000, now Pat. No. 7,078,395.

(60) Provisional application No. 60/139,520, filed on Jun. 16, 1999.

(30) Foreign Application Priority Data

| Apr. 30, 1999 | (GB) | ................................ | 9910166.9 |
| Jan. 28, 2000 | (GB) | ................................ | 0002113.9 |

(51) Int. Cl.
A61K 31/56 (2006.01)
A61K 31/33 (2006.01)
A01N 43/00 (2006.01)

(52) U.S. Cl. .................. 514/183; 514/178; 514/182

(58) Field of Classification Search .............. 514/183, 514/178, 182
See application file for complete search history.

(56) References Cited

U.S. PATENT DOCUMENTS

| 5,281,587 | A | 1/1994 | Reed |
| 5,616,574 | A | 4/1997 | Reed et al. |
| 5,763,492 | A | 6/1998 | Johnson et al. |
| 6,476,011 | B1 | 11/2002 | Reed et al. |
| 2003/0086924 | A1 | 5/2003 | Sliwkowski |

FOREIGN PATENT DOCUMENTS

| EP | 0 934 949 | 8/1999 |
| WO | 93/05063 | 3/1993 |
| WO | 93/05064 | 3/1993 |
| WO | WO 97/30041 | 8/1997 |
| WO | WO 97/32872 | 9/1997 |
| WO | WO 98/11124 | 3/1998 |
| WO | WO 98/24802 | 6/1998 |
| WO | WO 99/03876 | 1/1999 |
| WO | 99/27935 | 6/1999 |
| WO | 99/27936 | 6/1999 |
| WO | 99/64013 | 12/1999 |
| WO | 00/76487 | 12/2000 |

OTHER PUBLICATIONS

Gura et. al., Science (1997), 278:1041-1042.*
Johnson et. al., British Journal of Cancer (2001) 84:1424-1431.*
Martindale: The Complete Drug Reference, 32$^{nd}$ edition, Tumour Necrosis Factor, 1999, p. 568.
Purohit A et al: Metabolic Medicine, vol. 85, 2000, pp. 584-589.
Purohit et al. "Recent advances in the development of steroid sulphatase inhibitors." J. Steroid Biochem. Molec. Biol. 69:22-7238 (1999).
Purohit et al. "The development of A-ring modified analogues of oestrone3-O-sulphamate as potent steroid sulphatase inhibitors with reduced oestrogenicity." J. Steroid Biochem. Molec. Biol. 64(5-6):269-275 (1998).
Purohit et al. "Inhibition of tumor necrosis factorα-stimulated aromatase activity by microtubul⊖stabilizing agents, paclitaxel and 2-methoxyestradiol." Biochemical and Biophysical Research Comm. 261:214217 (1999).
Woo et al. "Active site directed inhibition of estrone sulfatase by nonsteroidal camarin sulfamates." J. Med. Chem. 39:1349-1352 (1996).
Schwarz et al. "Synthesis of estrogen sulfamates: compounds with a novel endocrinological profile." Steroids 61:710717 (1996).
Cushman et al. "Synthesis, antitubulin and antimitotic actrity, and cytotoxicity of analogs of 2-methoxyestradiol, an endogenous mammalian metabolite of estradiol that inhibits tubulin polymerization by binding to the colchicines binding site." J. Med. Chem. 38:204-2049 (1995).

(Continued)

*Primary Examiner* — Marcos Sznaidman
(74) *Attorney, Agent, or Firm* — Frommer, Lawrence & Haug LLP; Sandra Kuzmich, Esq.; Russell A. Garman

(57) ABSTRACT

There is provided use of a cyclic compound or a pharmaceutically active salt thereof in the manufacture of a medicament to prevent and/or inhibit and/or arrest cell cycling, wherein the cyclic compound comprises at least one ring, wherein Group I and Group II, independently of each other, are attached to a ring of the cyclic compound;

Figure 1:
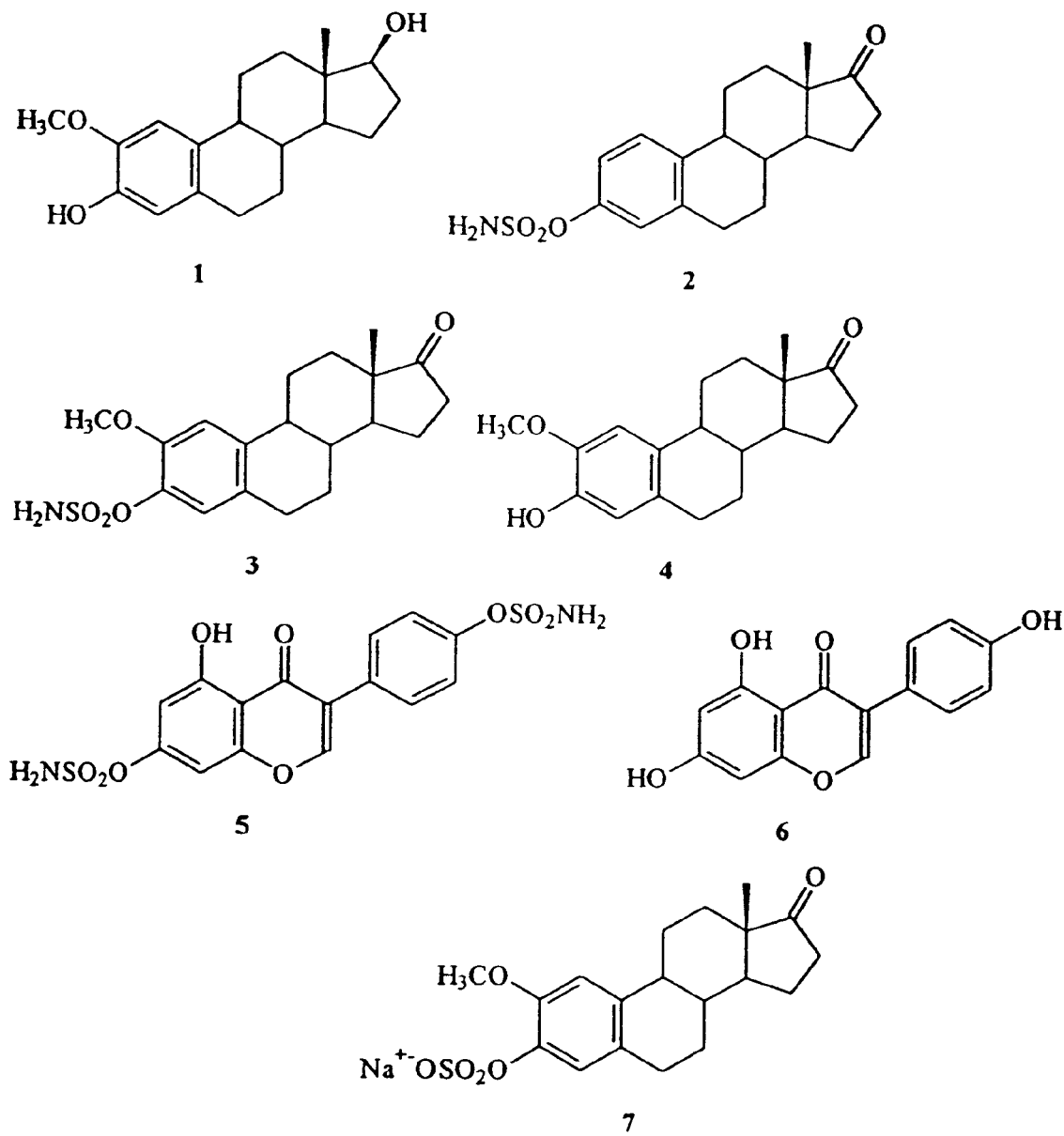

wherein Group I is a hydrocarbyl or an oxyhydrocarbyl group; and wherein Group II is a group of the formula

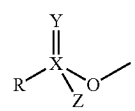

X is P or S;
when X is P, Y is =O or S, Z is —OH and R is hydrocarbyl or H;
when X is S, Y is =O, Z is =O, and R is hydrocarbyl or N(R$_1$)(R$_2$), wherein each of R$_1$ and R$_2$ is independently selected from H or a hydrocarbyl group.

17 Claims, 16 Drawing Sheets

OTHER PUBLICATIONS

Klauber et al. "Inhibition of angiogenesis and breast cancer in mice by the microtubule inhibitors 2-methoxyestradiol and taxol." Cancer Research 57:81-86 (1997).

Woo et al. "Oestrone-3-O-(N-acetyl)sulphamate, a potential molecular probe of the active site of oestrone sulphatse." Bioorganic & Medicinal Chemistry Letters 7(24):3075-3080 (1997).

Leese M et al: J. Med Chem., 2005, 48(16), pp. 5243-5256.

Kossodo, et al. *Changes in endogenous cytokines, adhesion molecules and platelets during cytokine-induced tumor necrosis*, British Journal of Cancer, 1995, vol. 72, p. 1165-1172.

Budd, et al. *A Southwest Oncology Group Phase II Trial of Recombinant Tumor Necrosis Factor in Metastatic Breast Cancer*, Cancer, 1991, vol. 68, No. 8, p. 1694-1695.

* cited by examiner

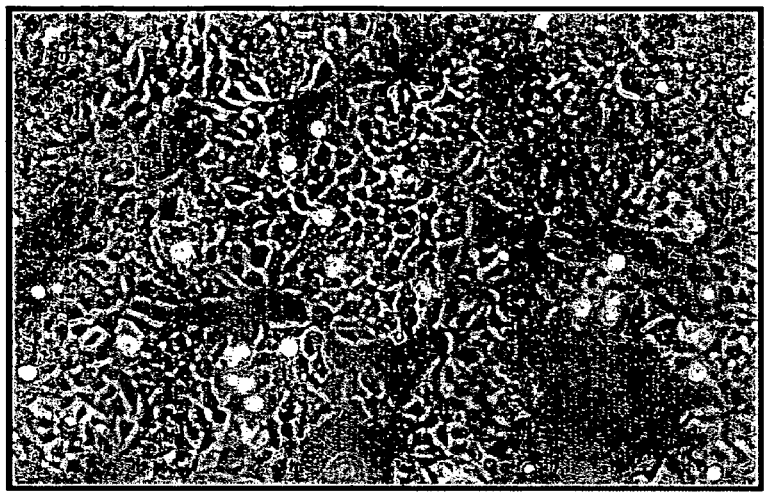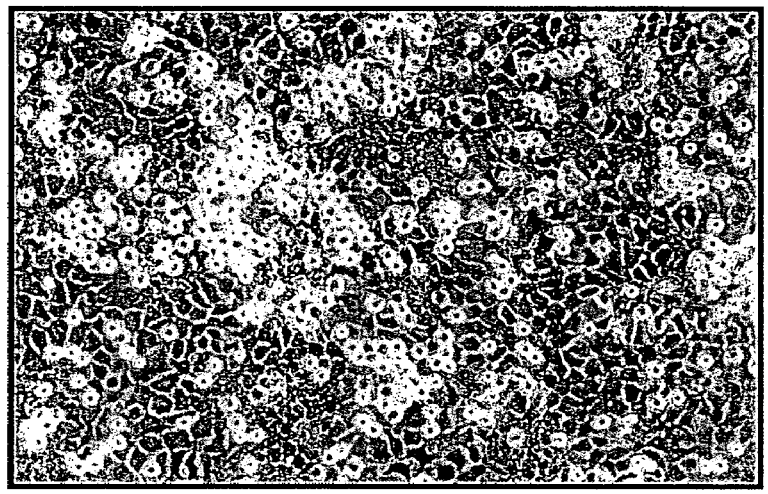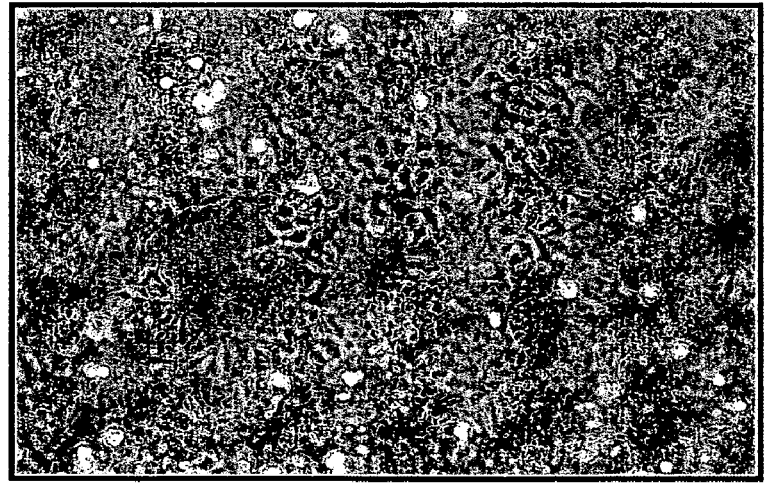
FIG. 3

Synthesis of 2-ethyloestrone 3-O-sulphamate (11); (i) $AlCl_3$/AcCl, $CH_3NO_2$, 5 h, (ii) HBr/AcOH, Δ 2h, (iii) $H_2$/Pd-C (10%), THF/EtOH, 50 psi, 24h, (iv) $AlCl_3$/NaI; DCM/$CH_3CN$; Δ 5h, (v) NaH (1.2 eq.)/ DMF, $ClSO_2NH_2$, $N_2$, 12 h and (vi) $NaBH_4$/THF/IPA, 16 h.

METHODS FOR TREATING OR PREVENTING CANCER BY PREVENTING, INHIBITING, OR ARRESTING CELL CYCLING

This application a divisional of U.S. patent application Ser. No. 09/561,453, filed Apr. 28, 2000 now U.S. Pat. No. 7,078,395, now allowed, which is based upon and claims priority from U.S. application Ser. No. 60/139,520, filed Jun. 16, 1999, U.K. application No. 0002113.9, filed Jan. 28, 2000, and U.K. application No. 9910166.9, filed Apr. 30, 1999. Each of the foregoing applications, and each document cited or referenced in each of the foregoing applications ("application cited documents") and each document referenced or cited in each of the application cited documents, as well as each document referenced or cited herein ("herein cited documents") and each document referenced or cited in herein cited documents, are hereby incorporated herein by reference.

The present invention relates to a method and a use. In particular the present invention relates to a method for the manufacture of a medicament.

As discussed in "Molecular Cell Biology" 3rd Ed. Lodish et al. pages 177-181 different eukaryotic cells can grow and divide at quite different rates. Yeast cells, for example, can divide every 120 min., and the first divisions of fertilised eggs in the embryonic cells of sea urchins and insects take only 1530 min. because one large pre-existing cell is subdivided. However, most growing plant and animal cells take 10-20 hours to double in number, and some duplicate at a much slower rate. Many cells in adults, such as nerve cells and striated muscle cells, do not divide at all; others, like the fibroblasts that assist in healing wounds, grow on demand but are otherwise quiescent.

Still, every eukaryotic cell that divides must be ready to donate equal genetic material to two daughter cells. DNA synthesis in eukaryotes does not occur throughout the cell division cycle but is restricted to a part of it before cell division.

The relationship between eukaryotic DNA synthesis and cell division has been thoroughly analysed in cultures of mammalian cells that were all capable of growth and division. In contrast to bacteria, it was found, eukaryotic cells spend only a part of their time in DNA synthesis, and it is completed hours before cell division (mitosis). Thus a gap of time occurs after DNA synthesis and before cell division; another gap was found to occur after division and before the next round of DNA synthesis. This analysis led to the conclusion that the eukaryotic cell cycle consists of an M (mitotic) phase, a $G_1$ phase (the first gap), the S (DNA synthesis) phase, a $G_2$ phase (the second gap), and back to M. The phases between mitoses ($G_1$, S, and $G_2$) are known collectively as the interphase.

Many nondividing cells in tissues (for example, all quiescent fibroblasts) suspend the cycle after mitosis and just prior to DNA synthesis; such "resting" cells are said to have exited from the cell cycle and to be in the $G_0$ state.

It is possible to identify cells when they are in one of the three interphase stages of the cell cycle, by using a fluorescence-activated cell sorter (FACS) to measure their relative DNA content: a cell that is in $G_1$ (before DNA synthesis) has a defined amount x of DNA; during S (DNA replication), it has between x and 2x; and when in $G_2$ (or M), it has 2x of DNA.

The stages of mitosis and cytokinesis in an animal cell are as follows (a) Interphase. The $G_2$ stage of interphase immediately precedes the beginning of mitosis. Chromosomal DNA has been replicated and bound to protein during the S phase, but chromosomes are not yet seen as distinct structures. The nucleolus is the only nuclear substructure that is visible under light microscope. In a diploid cell before DNA replication there are two morphologic chromosomes of each type, and the cell is said to be 2n. In $G_2$, after DNA replication, the cell is 4n. There are four copies of each chromosomal DNA. Since the sister chromosomes have not yet separated from each other, they are called sister chromatids.

b) Early prophase. Centrioles, each with a newly formed daughter centriole, begin moving toward opposite poles of the cell; the chromosomes can be seen as long threads. The nuclear membrane begins to disaggregate into small vesicles.

(c) Middle and late prophase. Chromosome condensation is completed; each visible chromosome structure is composed of two chromatids held together at their centromeres. Each chromatid contains one of the two newly replicated daughter DNA molecules. The microtubular spindle begins to radiate from the regions just adjacent to the centrioles, which are moving closer to their poles. Some spindle fibres reach from pole to pole; most go to chromatids and attach at kinetochores.

(d) Metaphase. The chromosomes move toward the equator of the cell, where they become aligned in the equatorial plane. The sister chromatids have not yet separated.

(e) Anaphase. The two sister chromatids separate into independent chromosomes. Each contains a centromere that is linked by a spindle fibre to one pole, to which it moves. Thus one copy of each chromosome is donated to each daughter cell. Simultaneously, the cell elongates, as do the pole-to-pole spindles. Cytokinesis begins as the cleavage furrow starts to form.

(f) Telophase. New membranes form around the daughter nuclei; the chromosomes uncoil and become less distinct, the nucleolus becomes visible again, and the nuclear membrane forms around each daughter nucleus. Cytokinesis is nearly complete, and the spindle disappears as the microtubules and other fibres depolymerise. Throughout mitosis the "daughter" centriole at each pole grows until it is full-length. At telophase the duplication of each of the original centrioles is completed, and new daughter centrioles will be generated during the next interphase.

(g) Interphase. Upon the completion of cytokinesis, the cell enters the $G_1$ phase of the cell cycle and proceeds again around the cycle.

It will be appreciated that cell cycling is an extremely important cell process. Deviations from normal cell cycling can result in a number of medical disorders. Increased and/or unrestricted cell cycling may result in cancer. Reduced cell cycling may result in degenerative conditions.

Cancer remains a major cause of mortality in most Western countries. Cancer therapies developed so far have included blocking the action or synthesis of hormones to inhibit the growth of hormone-dependent tumours. However, more aggressive chemotherapy is currently employed for the treatment of hormone-independent tumours.

Hence, the development of a pharmaceutical for anti-cancer treatment of hormone dependent and/or hormone independent tumours, yet lacking some or all of the side-effects associated with chemotherapy, would represent a major therapeutic advance.

The present invention seeks to provide a composition suitable for use in the treatment of cancers and, especially, breast cancer.

The following abbreviations used in the present specification have the given meanings:
E1S oestrone sulphate;
2-MeOE2,2-methoxyoestradiol;
2-OHE2,2-hydroxyoestradiol;
EMATE, oestrone-3-O-sulphamate;
2-MeOEMATE, 2-methoxyoestrone-3-O-sulphamate;
2-MeOE1,2-methoxyoestrone;
GenMATE, genistein-bis-sulphamate;
2-MeOE1S, 2-methoxyoestrone sulphate;
ER, estrogen receptor;
Tdt, terminal deoxynucleotidyl transferase;
TUNEL, Tdt-mediated dUTP-nick end labelling.

Oestrogens undergo a number of hydroxylation and conjugation reactions after their synthesis. Until recently it was thought that such reactions were part of a metabolic process that ultimately rendered oestrogens water soluble and enhanced their elimination from the body. It is now evident that some hydroxy metabolites (e.g. 2-hydroxy and 16α-hydroxy) and conjugates (e.g. oestrone sulphate, E1S) are important in determining some of the complex actions that oestrogens have in the body (1, 2).

Bradlow and his colleagues have investigated the formation of 2- and 16α-hydroxylated oestrogens in relation to conditions that alter the risk of breast cancer. There is now evidence that factors which increase 2-hydroxylase activity are associated with a reduced cancer risk, while those increasing 16α-hydroxylation may enhance the risk of breast cancer (3-6). Further interest in the biological role of estrogen metabolites has been stimulated by the growing body of evidence that 2-methoxyoestradiol (FIG. 1, 1, 2-MeOE2) is an endogenous metabolite with anti-mitotic properties (7). 2-MeOE2 is formed from 2-hydroxy estradiol (2-OHE2) by catechol estrogen methyl transferase, an enzyme that is widely distributed throughout the body.

Seegers and her colleagues originally reported that relatively high concentrations of 2-MeOE2 ($\geq 1$ μm) were cytotoxic to MCF-7 breast cancer cells (8). They also observed that 2-MeOE2 caused uneven chromosome distribution in cells which also had a disorientated microtubule structure. A subsequent study revealed that 2-MeOE2 had no effect on the morphology of normal human skin fibroblasts, but a marked effect on transformed fibroblasts (9).

In vivo 2-MeOE2 inhibits the growth of tumours arising from the subcutaneous injection of Meth A sarcoma, B16 melanoma or MDA-MB-435 estrogen receptor negative (ER−) breast cancer cells (10, 11). It also inhibits endothelial cell proliferation and migration, and in vitro angiogenesis. It was suggested that the ability of 2-MeOE2 to inhibit tumour growth in vivo may be due to its ability to inhibit tumour-induced angiogenesis rather than direct inhibition of the proliferation of tumour cells (10).

The mechanism by which 2-MeOE2 exerts its potent anti-mitogenic and anti-angiogenic effects is still being elucidated. There is evidence that at high concentrations it can inhibit microtubule polymerisation and act as a weak inhibitor of colchicine binding to tubulin (12). Recently, however, at concentrations that block mitosis, tubulin filaments in cells were not found to be depolymerised but to have an identical morphology to that seen after taxol treatment (13). It is possible, therefore, that like taxol, a drug that is used for breast and ovarian breast cancer therapy, 2-MeOE2 acts by stabilising microtubule dynamics.

While the identification of 2-MeOE2 as a new therapy for cancer represents an important advance, the bioavailability of orally administered oestrogens is poor. Furthermore, they can undergo extensive metabolism during their first pass through the liver. As part of a research programme to develop a steroid sulphatase inhibitor for breast cancer therapy, oestrone-3-O-sulphamate (FIG. 1, 2, EMATE) was identified as a potent active site-directed inhibitor (14, 15). Unexpectedly, EMATE proved to possess potent oestrogenic properties with its oral uterotrophic activity in rats being a 100-times higher than that of estradiol (16). Its enhanced oestrogenicity is thought to result from its absorption by red blood cells (rbcs) which protects it from inactivation during its passage through the liver and which act as a reservoir for its slow release for a prolonged period of time (17). A number of A-ring modified analogues were synthesised and tested, including 2-methoxy-oestrone-3-O-sulphamate (3,2-MeOEMATE) (18, 19). While this compound was equipotent with EMATE as a steroid sulphatase inhibitor, it was devoid of oestrogenicity.

The present invention seeks to provide a method of treatment of a cell cycling disorder. In particular, the present invention seeks to provide a method of treatment of cancer.

Aspects of the invention are defined in the appended claims.

The present invention is advantageous in that it provides a compound suitable for use in the treatment of cell cycling disorders such as cancers, including hormone dependent and hormone independent cancers.

In addition, the present invention is advantageous in that it provides a compound that is suitable for use in the treatment of cancers such as breast cancer, ovarian cancer, endometrial cancer, sarcomas, melanomas, prostate cancer, pancreatic cancer etc. and other solid tumours.

We have identified the effects that the compounds of the present invention such as 2-MeOEMATE, have on the proliferation of breast cancer cells and fibroblasts, and their effect on the cell cycle. In a preliminary in vivo study 2-MeOEMATE was found to cause the rapid regression of nitrosomethylurea (NMU)-induced mammary tumours in intact rats.

In accordance with the present invention cell cycling is inhibited and/or prevented and/or arrested. Preferably cell cycling is prevented and/or arrested.

In a preferred aspect cell cycling is inhibited and/or prevented and/or arrested in the $G_2/M$ phase.

In a preferred aspect cell cycling is irreversibly prevented and/or inhibited and/or arrested. Preferably cell cycling is irreversibly prevented and/or arrested.

By the term "irreversibly prevented and/or inhibited and/or arrested" it is meant after application of a compound of the present invention, on removal of the compound the effects of the compound, namely prevention and/or inhibition and/or arrest of cell cycling, are still observable. More particularly by the term "irreversibly prevented and/or inhibited and/or arrested" it is meant that when assayed in accordance with Protocol I, cells treated with a compound of interest show less growth after Stage 2 of Protocol I than control cells. Protocol I is recited after the Examples.

The compound of the present invention is a cyclic compound comprising at least one ring, wherein Group I and Group II, independently of each other, are attached to a ring of the cyclic compound; wherein Group I is a hydrocarbyl or an oxyhydrocarbyl group; and wherein Group II is a group of the formula

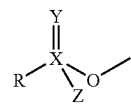

X is P or S; when X is P, Y is =O or S, Z is —OH and R is hydrocarbyl or H; when X is S, Y is =O, Z is =O, and R is hydrocarbyl or $N(R_1)(R_2)$, wherein each of $R_1$ and $R_2$ is independently selected from H or a hydrocarbyl group.

The term "hydrocarbyl group" as used herein means a group comprising at least C and H and may optionally comprise one or more other suitable substituents. Examples of such substituents may include halo-, alkoxy-, nitro-, a hydrocarbon group, an N-acyl group, a cyclic group etc. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the hydrocarbyl group may contain hetero atoms. Suitable hetero atoms will be apparent to those skilled in the art and include, for instance, sulphur, nitrogen and oxygen.

In one preferred embodiment of the present invention, the hydrocarbyl group is a hydrocarbon group.

Here the term "hydrocarbon" means any one of an alkyl group, an alkenyl group, an alkynyl group, an acyl group, which groups may be linear, branched or cyclic, or an aryl group. The term hydrocarbon also includes those groups but wherein they have been optionally substituted. If the hydrocarbon is a branched structure having substituent(s) thereon, then the substitution may be on either the hydrocarbon backbone or on the branch; alternatively the substitutions may be on the hydrocarbon backbone and on the branch.

The compound is a cyclic compound. In this regard, the compound can be a single ring compound or a polycyclic compound. Here, the term "polycyclic" includes fused and non-fused ring structures including combinations thereof.

The cyclic group may be a single ring or it is a polycyclic ring structure.

In one aspect, the cyclic group may contain any one or more of C, H, O, N, P, halogen (including Cl, Br and I), S and P.

At least one of the cyclic groups may be a heterocyclic group (a heterocycle) or a non-heterocyclic group.

At least one of the cyclic groups may be a saturated ring structure or an unsaturated ring structure (such as an aryl group).

Preferably, at least one of the cyclic groups is an aryl ring.

Preferably, Group I and/or Group II is linked or attached to the aryl ring.

If the cyclic group is polycyclic some or all of the ring components of the compound may be fused together or joined via one or more suitable spacer groups.

The polycyclic compound may comprise a number of fused rings. In this aspect the fused rings may comprise any combination of different size rings, such as 3 six-membered rings (6,6,6), a six-membered ring, a seven-membered ring and a six-membered ring (6,7,6), a six-membered ring and two eight-membered rings (6,8,8) etc.

In one aspect the present invention relates to compounds wherein the polycyclic compounds are other than (6,6,7) rings. In a further aspect, the present invention relates to compounds wherein the polycyclic compounds only contain rings having other than 7 members.

In one aspect, if the cyclic group is polycyclic, Group I and Group II are each attached to the same ring of the polycyclic compound.

Thus, in accordance with one aspect of the present invention, preferably the compound is a polycyclic compound.

Preferably the polycyclic compound will contain, inclusive of all substituents, no more than 50 about carbon atoms, more usually no more than about 30 to 40 carbon atoms.

The polycyclic compound can comprise at least two ring components, or at least three ring components, or at least four ring components.

Preferably, the polycyclic compound comprises four ring components.

Preferred polycyclic compounds have a steroidal ring component—that is to say a cyclopentanophenanthrene skeleton, or bio-isosteres thereof.

As is well known in the art, a classical steroidal ring structure has the generic formula of:

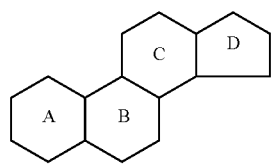

In the above formula, the rings have been labelled in the conventional manner.

An example of a bio-isostere is when any one or more of rings A, B, C and D is a heterocyclic ring and/or when any one or more of rings A, B, C and D has been substituted and/or when any one or more of rings A, B, C and D has been modified; but wherein the bio-isostere in the absence of the sulphamate group has steroidal properties.

In this regard, the structure of a preferred polycyclic compound can be presented as:

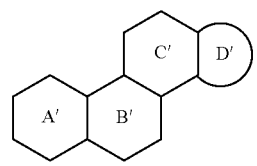

wherein each ring A', B', C' and D' independently represents a heterocyclic ring or a non-heterocyclic ring, which rings may be independently substituted or unsubstituted, saturated or unsaturated.

By way of example, any one or more of rings A', B', C' and D' may be independently substituted with suitable groups—such as an alkyl group, an aryl group, a hydroxy group, a halo group, a hydrocarbyl group, an oxyhydrocarbyl group etc.

An example of D' is a five or six membered non-heterocyclic ring having at least one substituent.

In one preferred embodiment, the ring D' is substituted with a ethinyl group.

If any one of rings A', B', C' and D' is a heterocyclic ring, then preferably that heterocyclic ring comprises a combination of C atoms and at least one N atom and/or at least one O atom. Other heterocyclic atoms may be present in the ring.

Examples of suitable, preferred steroidal nuclei rings A'-D' of the compounds of the present invention include rings A-D of dehydroepiandrosterone and oestrogens including oestrone.

Preferred steroidal nuclei rings A'-D' of the compounds of the present invention include rings A-D of:

Oestrones and Substituted Oestrones, viz:
oestrone
4-OH-oestrone
6α-OH-oestrone
7α-OH-oestrone
16α-OH-oestrone
16β-OH-oestrone
17-deoxyoestrone
oestrone Oestradiols and Substituted Oestradiols, viz:
4-OH-17β-oestradiol
6α-OH-17β-oestradiol
7α-OH-17β-oestradiol
4-OH-17α-oestradiol
6α-OH-17α-oestradiol
7α-OH-17α-oestradiol
16α-OH-17α-oestradiol
16α-OH-17β-oestradiol
16β-OH-17α-oestradiol
16β-OH-17β-oestradiol
17α-oestradiol
17β-oestradiol
17α-ethinyl-17β-oestradiol
17β-ethinyl-17α-oestradiol
17-deoxyoestradiol Oestriols and substituted Oestriols, viz:
oestriol
4-OH-oestriol
6α-OH-oestriol
7α-OH-oestriol
17-deoxyoestriol Dehydroepiandrosterones and Substituted Dehydroepiandrosterones, viz:
dehydroepiandrosterones
6α-OH-dehydroepiandrosterone
7α-OH-dehydroepiandrosterone
16α-OH-dehydroepiandrosterone
16β-OH-dehydroepiandrosterone In general terms the ring system A'B'C'D' may contain a variety of non-interfering substituents. In particular, the ring system A'B'C'D' may contain one or more hydroxy, alkyl especially lower ($C_1$-$C_6$) alkyl, e.g. methyl, ethyl, n-propyl, isopropyl, n-butyl, sec-butyl, tert-butyl, n-pentyl and other pentyl isomers, and n-hexyl and other hexyl isomers, alkoxy especially lower ($C_1$-$C_6$) alkoxy, e.g. methoxy, ethoxy, propoxy etc., alkinyl, e.g. ethinyl, or halogen, e.g. fluoro substituents.

In an alternative embodiment, the polycyclic compound may not contain or be based on a steroid nucleus. In this regard, the polycyclic compound may contain or be based on a non-steroidal ring system—such as diethylstilboestrol, stilboestrol, coumarins, flavonoids, combrestatin and other ring systems. Other suitable non-steroidal compounds for use in or as the composition of the present invention may be found in U.S. Pat. No. 5,567,831.

Preferably, Group I and Group II are each attached to the same ring of the cyclic compound of the present invention at positions ortho with respect to each other.

Preferably, the polycyclic compound has a steroidal structure and Group I is attached to the A ring.

Preferably, the Group I is attached to the 2 position of the A ring of the steroidal structure.

Preferably, the polycyclic compound has a steroidal structure and Group II is attached to the A ring.

Preferably, the Group II is attached to the 3 position of the A ring of the steroidal structure.

Group I is a hydrocarbyl or an oxyhydrocarbyl group.

The term "hydrocarbyl group" as used herein is defined above.

In one preferred embodiment of the present invention, the hydrocarbyl group is a hydrocarbon group.

The term "hydrocarbon group" as used herein is defined above.

Preferably the hydrocarbyl group is of the formula $C_{1-6}$ (such as a $C_{1-3}$).

If the compound comprises a steroidal nucleus, preferably the A ring has a hydrocarbyl group at the 2 position.

More preferably the group $C_{1-6}$ is attached to the 2 position of the A ring of a steroidal nucleus.

Preferably, the hydrocarbyl group is an alkyl.

The alkyl is preferably a lower alkyl group containing from 1 to 5 carbon atoms, that is to say methyl, ethyl, propyl etc. Preferably, the alkyl group is methyl or ethyl.

Thus, in a preferred embodiment, if the compound comprises a steroidal nucleus the A ring has an methyl or ethyl substituent at the 2 position.

The term "oxyhydrocarbyl group" as used herein means a group comprising at least C, H and O and may optionally comprise one or more other suitable substituents. Examples of such substituents may include halo-, alkoxy-, nitro-, an alkyl group, a cyclic group etc. In addition to the possibility of the substituents being a cyclic group, a combination of substituents may form a cyclic group. If the oxyhydrocarbyl group comprises more than one C then those carbons need not necessarily be linked to each other. For example, at least two of the carbons may be linked via a suitable element or group. Thus, the oxyhydrocarbyl group may contain hetero atoms. Suitable hetero atoms will be apparent to those skilled in the art and include, for instance, sulphur and nitrogen.

In one preferred embodiment of the present invention, the oxyhydrocarbyl group is a oxyhydrocarbon group.

Here the term "oxyhydrocarbon" means any one of an alkoxy group, an oxyalkenyl group, an oxyalkynyl group, which groups may be linear, branched or cyclic, or an oxyaryl group. The term oxyhydrocarbon also includes those groups but wherein they have been optionally substituted. If the oxyhydrocarbon is a branched structure having substituent(s) thereon, then the substitution may be on either the hydrocarbon backbone or on the branch; alternatively the substitutions may be on the hydrocarbon backbone and on the branch.

Preferably the oxyhydrocarbyl group is of the formula $C_{1-6}O$ (such as a $C_{1-3}O$).

If the compound comprises a steroidal nucleus, preferably the A ring has an oxyhydrocarbyl group at the 2 position.

More preferably the group $C_{1-6}O$ is attached to the 2 position of the A ring of a steroidal nucleus.

Preferably, the oxyhydrocarbyl group is an alkoxy.

The alkyl group of the alkoxy substituent is preferably a lower alkyl group containing from 1 to 5 carbon atoms, that is to say methyl, ethyl, propyl etc. Preferably, the alkyl group is methyl.

Thus, in a preferred embodiment, if the compound comprises a steroidal nucleus the A ring has an methoxy substituent at the 2 position.

In one preferred embodiment of the present invention, preferably the compound is non-oestrogenic. The term "non-oestrogenic" means exhibiting no or substantially no oestrogenic activity.

In one preferred embodiment of the present invention, preferably the compound is not capable of being metabolised to compounds which display or induce hormonal activity.

In one preferred embodiment of the present invention, preferably the compound of the present invention is orally active.

The present invention is based on the highly surprising finding the compounds of the present invention provides an effective means to prevent and/or inhibit and/or arrest cell cycling.

We have found that compounds having a hydrocarbyl or an oxyhydrocarbyl substituent on the A ring and/or having a group of the formula of Group II on the A ring are potent (and in some cases highly potent) in preventing and/or inhibiting and/or arresting cell cycling.

A preferred compound of the present invention has the formula:

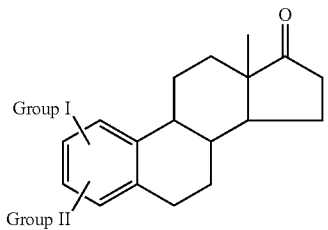

wherein rings A, B, C and D are independently optionally substituted.

Preferably Group I is in the 2-position.
Preferably Group II is in the 3-position.
In one preferred aspect, X is S and R is $N(R_1)(R_2)$. In other words, preferably Group II is a group of the formula:

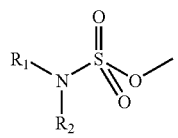

wherein each of $R_1$ and $R_2$ is independently selected from H or a hydrocarbyl group.

Thus in a preferred aspect, the present invention provides the use of a cyclic compound or a pharmaceutically active salt thereof in the manufacture of a medicament to prevent and/or inhibit and/or arrest cell cycling, wherein the cyclic compound comprises at least one ring, wherein Group I and Group II, independently of each other, are attached to a ring of the cyclic compound; wherein Group I is a hydrocarbyl or an oxyhydrocarbyl group; and wherein Group II is a group of the formula

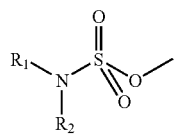

wherein each of $R_1$ and $R_2$ is independently selected from H or a hydrocarbyl group.

Group II of these preferred compounds is referred to as a "sulphamate group". These preferred compounds are referred to as "sulphamate compounds".

Preferably, $R_1$ and $R_2$ are independently selected from H or alkyl, cycloalkyl, alkenyl and aryl, or together represent alkylene, wherein the or each alkyl or cycloalkyl or alkenyl or optionally contain one or more hetero atoms or groups.

When substituted, the N-substituted sulphamate compound may contain one or two N-alkyl, N-alkenyl, N-cycloalkyl, N-acyl, or N-aryl substituents, preferably containing or each containing a maximum of 10 carbon atoms. When $R_1$ and/or $R_2$ is alkyl, the preferred values are those where $R_1$ and $R_2$ are each independently selected from lower alkyl groups containing from 1 to 5 carbon atoms, that is to say methyl, ethyl, propyl etc. Preferably $R_1$ and $R_2$ are both methyl. When $R_1$ and/or $R_2$ is aryl, typical values are phenyl and tolyl (—$PhCH_3$; o-, m- or p-). Where $R_1$ and $R_2$ represent cycloalkyl, typical values are cyclopropyl, cyclopentyl, cyclohexyl etc. When joined together $R_1$ and $R_2$ typically represent an alkylene group providing a chain of 4 to 6 carbon atoms, optionally interrupted by one or more hetero atoms or groups, e.g. -O- or —NH— to provide a 5-, 6- or 7-membered heterocycle, e.g. morpholino, pyrrolidino or piperidino.

Within the values alkyl, cycloalkyl, alkenyl, acyl and aryl we include substituted groups containing as substituents therein one or more groups which do not interfere with the cell cycling arresting and/or inhibiting and/or prevention activity of the compound in question. Exemplary non-interfering substituents include hydroxy, amino, halo, alkoxy, alkyl and aryl. A non-limiting example of a hydrocarbyl group is an acyl group.

In some preferred embodiments, at least one of $R_1$ and $R_2$ is H.

Examples of suitable sulphamate compounds for use in the present invention, or examples of suitable compounds that can be converted to suitable sulphamate compounds for use in the present invention, can be found in the art—such as PCT/GB92/01587, PCT/GB97/03352, PCT/GB97/00444, GB 9725749.7, GB 9725750.5, U.S. Pat. No. 5,567,831, U.S. Pat. No. 5,677,292, U.S. Pat. No. 5,567,831, WO-A-96/05216, and WO-A-96/05217.

By way of example, PCT/GB92/01587 teaches novel sulphamate compounds and pharmaceutical compositions containing them for use in the treatment of oestrone dependent tumours, especially breast cancer. These sulphamate compounds are sulphamate esters. Examples of such inhibitors are sulphamate ester derivatives of steroids.

Another compound suitable for use in the present invention has at least the following skeletal structure:

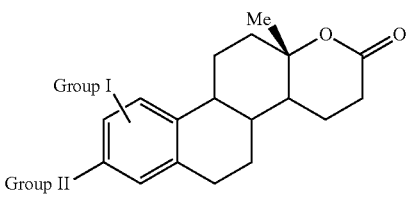

wherein Group II denotes a sulphamate group as described above; and rings A, B, C and D are independently optionally substituted.

Preferably, Group II is the above-mentioned preferred formula for the sulphamate group. In this regard, it is preferred that at least one of $R_1$ and $R_2$ is H.

Another compound suitable for use in the present invention has at least the following skeletal structure:

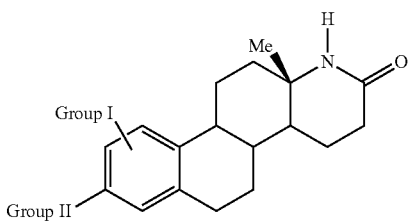

wherein Group II denotes a sulphamate group as described above; and rings A, B, C and D are independently optionally substituted.

Preferably, R is the above-mentioned preferred formula for the sulphamate group. In this regard, it is preferred that at least one of $R_1$ and $R_2$ is H.

We have found that compounds having an a sulphamate group on the A ring and a hydrocarbyl or an oxyhydrocarbyl substituent on the A ring are particularly potent (and in some cases highly potent) in preventing and/or inhibiting and/or arresting cell cycling.

A preferred compound of the present invention has the formula:

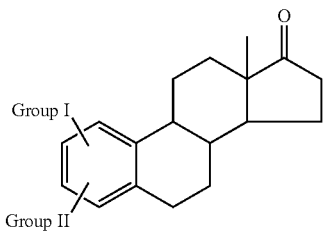

Group II is a sulphamate group; and rings A, B, C and D are independently optionally substituted.

Preferably Group I is in the 2-position.

Preferably Group II is in the 3-position.

For the present invention, preferably the sulphamate compound is an oxyhydrocarbyl steroidal sulphamate compound, in particular 2-methoxyoestrone-3-O-sulphamate, or a pharmaceutically active salt thereof, including analogues thereof.

2-methoxyoestrone-3-O-sulphamate is an analogue of oestrone-3-O-sulphamate (otherwise known as "EMATE"), which has the following structure:

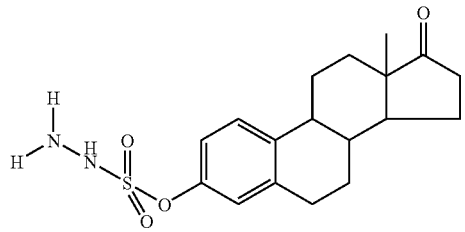

and can be called 2-methoxy EMATE.

2-methoxy EMATE is the sulphamoylated derivative of a naturally occurring oestrogen metabolite, 2-methoxyoestrone. This compound is formed in the liver by the hydroxylation of oestrone by a 2-hydroxylase, with subsequent metabolism to the methoxy derivative by catechol oestrogen methyl transferase.

2-methoxy EMATE has the formula presented as formula below:

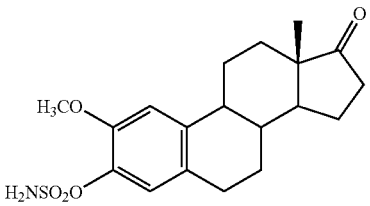

2-methoxy EMATE is believed to act in vivo, at least in part, by preventing and/or inhibiting and/or arresting cell cycling.

Thus, in a highly preferred embodiment the sulphamate compound is an oxyhydrocarbyl steroidal sulphamate compound, in particular 2-methoxyoestrone-3-O-sulphamate (2-methoxy EMATE).

In this regard, we have found that a sulphamate compound having a $C_{1-6}$ (such as a $C_{1-3}$) alkoxy substituent at the 2 position of the A ring, in particular 2-methoxy EMATE, is highly potent in preventing and/or inhibiting growth of tumours.

In one embodiment, preferably, the sulphamate compound is an oxyhydrocarbyl steroidal sulphamate compound wherein the sulphamate group is in the 3 position on the steroidal component and/or the oxyhydrocarbyl group is in the 2-position position on the steroidal component.

In one embodiment, preferably, the sulphamate compound is an oxyhydrocarbyl derivative of oestrone sulphamate.

In one embodiment, preferably, the sulphamate compound is an oxyhydrocarbyl derivative of oestrone-3-O-sulphamate.

In one embodiment, preferably, the sulphamate compound is a $C_{1-6}$ (such as a $C_{1-3}$) alkoxy derivative of oestrone-3-O-sulphamate.

In one embodiment, preferably, the sulphamate compound is a 2-$C_{1-6}$ (such as a $C_{1-3}$) alkoxy derivative of oestrone-3-O-sulphamate.

In one embodiment, preferably, the sulphamate compound is 2-methoxyoestrone-3-O-sulphamate.

For the present invention, the sulphamate compound may preferably be a hydrocarbyl steroidal sulphamate compound, in particular 2-ethyloestrone-3-O-sulphamate, or a pharmaceutically active salt thereof, including analogues thereof.

2-ethyloestrone-3-O-sulphamate is an analogue of oestrone-3-O-sulphamate and can be called 2-ethyl EMATE.

2-ethyl EMATE has the formula presented as formula below:

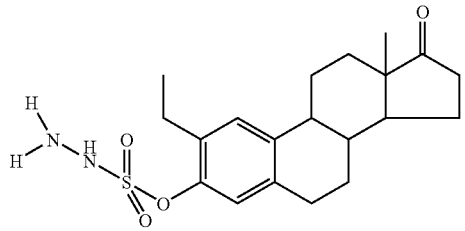

2-ethyl EMATE is believed to act in vivo, at least in part, by preventing and/or inhibiting and/or arresting cell cycling.

Thus, in a highly preferred embodiment the sulphamate compound is a hydrocarbyl steroidal sulphamate compound, in particular 2-ethyloestrone-3-O-sulphamate (2-ethyl EMATE).

In this regard, we have found that a sulphamate compound having a $C_{1-6}$ (such as a $C_{1-3}$) alkyl substituent at the 2 position of the A ring, in particular 2-ethyl EMATE, is highly potent in preventing and/or inhibiting growth of tumours.

In one embodiment, preferably, the sulphamate compound is a hydrocarbyl steroidal sulphamate compound wherein the sulphamate group is in the 3 position on the steroidal component and/or the hydrocarbyl group is in the 2-position position on the steroidal component.

In one embodiment, preferably, the sulphamate compound is a hydrocarbyl derivative of oestrone sulphamate.

In one embodiment, preferably, the sulphamate compound is a hydrocarbyl derivative of oestrone-3-O-sulphamate.

In one embodiment, preferably, the sulphamate compound is a $C_{1-6}$ (such as a $C_{1-3}$) alkyl derivative of oestrone-3-O-sulphamate.

In one embodiment, preferably, the sulphamate compound is a 2-$C_{1-6}$ (such as a $C_{1-3}$) alkyl derivative of oestrone-3-O-sulphamate.

In one embodiment, preferably, the sulphamate compound is 2-ethyloestrone-3-O-sulphamate.

The sulphamate compounds of the present invention may be prepared by reacting an appropriate alcohol with the appropriate sulphamoyl chloride, $R_1R_2NSO_2Cl$. Preferred conditions for carrying out the reaction are as follows. Sodium hydride and a sulphamoyl chloride are added to a stirred solution of the alcohol in anhydrous dimethyl formamide at 0° C. Subsequently, the reaction is allowed to warm to room temperature whereupon stirring is continued for a further 24 hours. The reaction mixture is poured onto a cold saturated solution of sodium bicarbonate and the resulting aqueous phase is extracted with dichloromethane. The combined organic extracts are dried over anhydrous $MgSO_4$. Filtration followed by solvent evaporation in vacuo and co-evaporated with toluene affords a crude residue which is further purified by flash chromatography. Preferably, the alcohol is derivatised, as appropriate, prior to reaction with the sulphamoyl chloride. Where necessary, functional groups in the alcohol may be protected in known manner and the protecting group or groups removed at the end of the reaction.

In one aspect of the present invention X is P, Y is =O and Z is —OH; or X is S; Y is =O, Z is =O, and R is hydrocarbyl. Alternatively stated, the present compound is a sulphonate or a phosphonate compound in which Group I is a group of the formula:

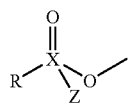

wherein X is P or S; when X is P, Z is —OH; when X is S, Z is =O; and R is hydrocarbyl.

Preferably the sulphonate or phosphonate compound is a polycyclic compound. More preferably the sulphonate or phosphonate compound has a steroidal structure.

When the sulphonate or phosphonate compound has a steroidal structure the sulphonate or phosphonate compound may have at least one sulphonate or phosphonate group attached to the 3 position of the A ring of the steroidal nucleus.

In a further preferred aspect the sulphonate or phosphonate compound comprises at least one hydrocarbon group, preferably $C_{1-6}$ alkyl, attached to the 2 position of the A ring of a steroidal nucleus.

Thus in a further aspect the present invention provides a sulphonate or a phosphonate compound comprising a steroidal ring and a sulphonate or a phosphonate group of the formula:

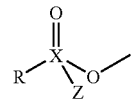

wherein
X is P or S;
when X is P, Z is —OH, and R is hydrocarbyl or H;
when X is S, Z is =O, and R is hydrocarbyl; and
wherein the sulphonate or phosphonate group is attached to the 3 position of the A ring of the steroidal nucleus; and at least one hydrocarbon group, preferably $C_{1-6}$ alkyl, is attached to the 2 position of the A ring of a steroidal nucleus.

These novel sulphonate or a phosphonate compounds may be used in medicine, preferably used in accordance with the present invention.

Examples of suitable sulphonate or a phosphonate compounds for use in the present invention, or examples of suitable compounds that can be converted to suitable sulphonate or a phosphonate compounds for use in or the present invention, can be found in the art—such as PCT/GB92/01586.

In a further aspect the present invention provides the use of a composition in the manufacture of a medicament to prevent and/or inhibit and/or arrest cell cycling, wherein the composition comprises
(i) a compound as defined herein; and
(ii) a further compound as defined herein; and/or
(iii) a pharmaceutically acceptable carrier, diluent, or excipient; and/or
(iv) a biological response modifier; and/or
(v) pure antioestrogens; and/or
(vi) selective estrogen response modifiers (SERMs); and/or
(vii) taxol.

The term biological response modifier ("BRM") includes cytokines, immune modulators, growth factors, haematopoiesis regulating factors, colony stimulating factors, chemotactic, hemolytic and thrombolytic factors, cell surface receptors, ligands, leukocyte adhesion molecules, monoclonal antibodies, preventative and therapeutic vaccines, hormones, extracellular matrix components, fibronectin, etc.

Preferably, the biological response modifier is a cytokine. Examples of cytokines include: interleukins (IL)—such as IL-1, IL-2, IL-3, IL-4, IL-5, IL-6, IL-7, IL-8, IL-9, IL-10, IL-11, IL-12, IL-19; Tumour Necrosis Factor (TNF)—such as TNF-α; Interferon alpha, beta and gamma; TGF-β.

Preferably the cytokine is tumour necrosis factor (TNF).

For the preferred aspect of the present invention, the TNF may be any type of TNF—such as TNF-α, TNF-β, including derivatives or mixtures thereof. More preferably the cytokine is TNF-α.

Teachings on TNF may be found in the art—such as WO-A-98/08870 and WO-A-98/13348.

For pharmaceutical administration, the composition of the present invention can be formulated in any suitable manner utilising conventional pharmaceutical formulating techniques and pharmaceutical carriers, adjuvants, excipients, diluents etc.—such as those for parenteral administration. Approximate effective dose rates are in the range 100 to 800 mg/day depending on the individual activities of the compounds in question and for a patient of average (70 Kg) bodyweight. More usual dosage rates for the preferred and more active compositions will be in the range 200 to 800 mg/day, more preferably, 200 to 500 mg/day, most preferably from 200 to 250 mg/day. They may be given in single dose regimes, split dose regimes and/or in multiple dose regimes lasting over several days. For oral administration they may be formulated in tablets, capsules, solution or suspension containing from 100 to 500 mg of composition per unit dose. Alternatively and preferably the compositions will be formulated for parenteral administration in a suitable parenterally administrable carrier and providing single daily dosage rates in the range 200 to 800 mg, preferably 200 to 500, more preferably 200 to 250 mg. Such effective daily doses will, however, vary depending on inherent activity of the active ingredient and on the bodyweight of the patient, such variations being within the skill and judgement of the physician.

The compound or composition of the present invention may be administered in any suitable manner—such as any one or more of oral administration, topical administration (such as by means of a patch), parenteral administration, rectal administration or by inhalation spray.

In the method of treatment, the subject is preferably a mammal, more preferably a human. For some applications, preferably the human is a woman.

For particular applications, it is envisaged that the compounds or compositions of the present invention may be used in combination therapies, either with a sulphatase inhibitor, or, for example, in combination with an aromatase inhibitor, such as for example, 4-hydroxyandrostenedione (4-OHA).

In accordance with the present invention, the components of the composition can be added in admixture, simultaneously or sequentially. Furthermore, in accordance with the present invention it may be possible to form at least a part of the composition in situ (such as in vivo) by inducing the expression of—or increasing the expression of—one of the components. For example, it may be possible to induce the expression of—or increase the expression of—the biological response modifier, such as TNF. By way of example, it may be possible to induce the expression of—or increase the expression of—TNF by adding bacterial lipopolysaccharide (LPS) and muramyl dipeptide (MDP). In this regard, bacterial LPS and MDP in combination can stimulate TNF production from murine spleen cells in vitro and tumour regression in vivo (Fuks et al Biull Eksp Biol Med 1987 104: 497-499).

The present invention also provides compositions/compounds which:

cause inhibition of growth of oestrogen receptor positive (ER+) and ER negative (ER−) breast cancer cells in vitro by preventing and/or inhibiting and/or arresting cell cycling.

cause regression of nitroso-methyl urea (NMU)-induced mammary tumours in intact animals (i.e. not ovariectomised).

prevent and/or inhibit and/or arrest cell cycling in cancer cells.

act in vivo by preventing and/or inhibiting and/or arresting cell cycling act as a cell cycling agonist.

In a further aspect the present invention provides use of a cyclic compound or a pharmaceutically active salt thereof in the manufacture of a cell cycling agonist, wherein the cyclic compound comprises at least one ring, wherein Group I and Group II, independently of each other, are attached to a ring of the cyclic compound; wherein Group I is a hydrocarbyl or an oxyhydrocarbyl group; and wherein Group II is a group of the formula

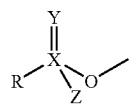

X is P or S; when X is P, Y is =O or S, Z is —OH and R is hydrocarbyl or H; when X is S, Y is =O, Z is =O, and R is hydrocarbyl or $N(R_1)(R_2)$, wherein each of $R_1$ and $R_2$ is independently selected from H or a hydrocarbyl group.

The compounds of the present invention such as 2-methoxyoestrogens are emerging as a new class of drug that can inhibit tumour growth and inhibit angiogenesis. As sulphamoylation of oestrogens enhances their potency and bioavailability we describe below the synthesis of 2-methoxyoestrone-3-O-sulphamate (2-MeOEMATE) and comparison of its ability to inhibit the proliferation of breast cancer cells with that of 2-methoxyoestrone (2-MeOE1). 2-MeOEMATE (1 μM) inhibited the growth of estrogen receptor positive MCF-7 breast cancer cells by 52% whereas 2-MeOE1 had little effect at this concentration. 2-MeOEMATE also inhibited the growth of estrogen receptor positive MDA-MB-231 breast cancer cells. Exposure of cells to 2-MeOEMATE caused them to round up and become detached suggesting that this compound may induce cells to undergo apoptosis. Cell cycle analysis revealed that 2-MeOEMATE caused cells to arrest in the $G_2/M$ phase with the increase in $G_2/M$ arrested cells being detectable by 12 h. Exposure of MCF-7 cells to 2MeOEMATE for 24 h followed by culture in drug-free medium for 24 h did not reverse the arrest of cells in the $G_2/M$ phase. TUNEL analysis confirmed that 2-MeOEMATE induced apoptosis in a significant proportion of treated MCF-7 cells. In an preliminary in vivo study, employing nitrosomethylurea-induced mammary tumours in intact rats, 2-MeOE1 (20 mg/kg/d, p.o. for 11 days) had little effect on tumour growth. In contrast, the same dose of 2-MeOEMATE resulted in the almost complete regression of ⅔ tumours over an 11-day period. It is concluded that 2-MeOEMATE should have considerable therapeutic potential for the treatment of hormone-dependent and independent breast tumours.

In summation, the present invention provides compositions for use in treatment of tumours and pharmaceutical compositions containing them.

The present invention will now be described only by way of example, in which reference, in which reference shall be made to the following Figures.

Figure 2:
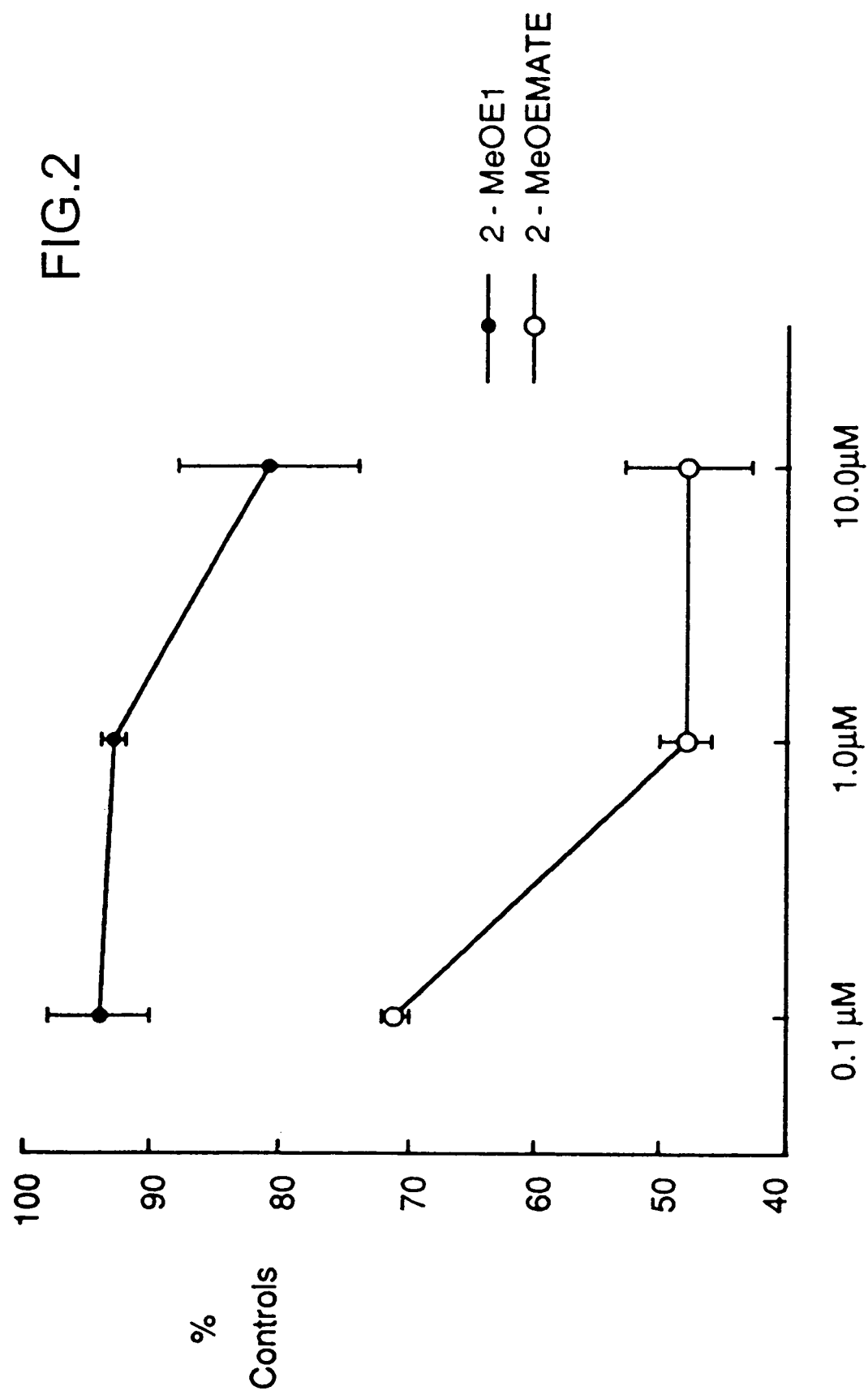
Figure 4:
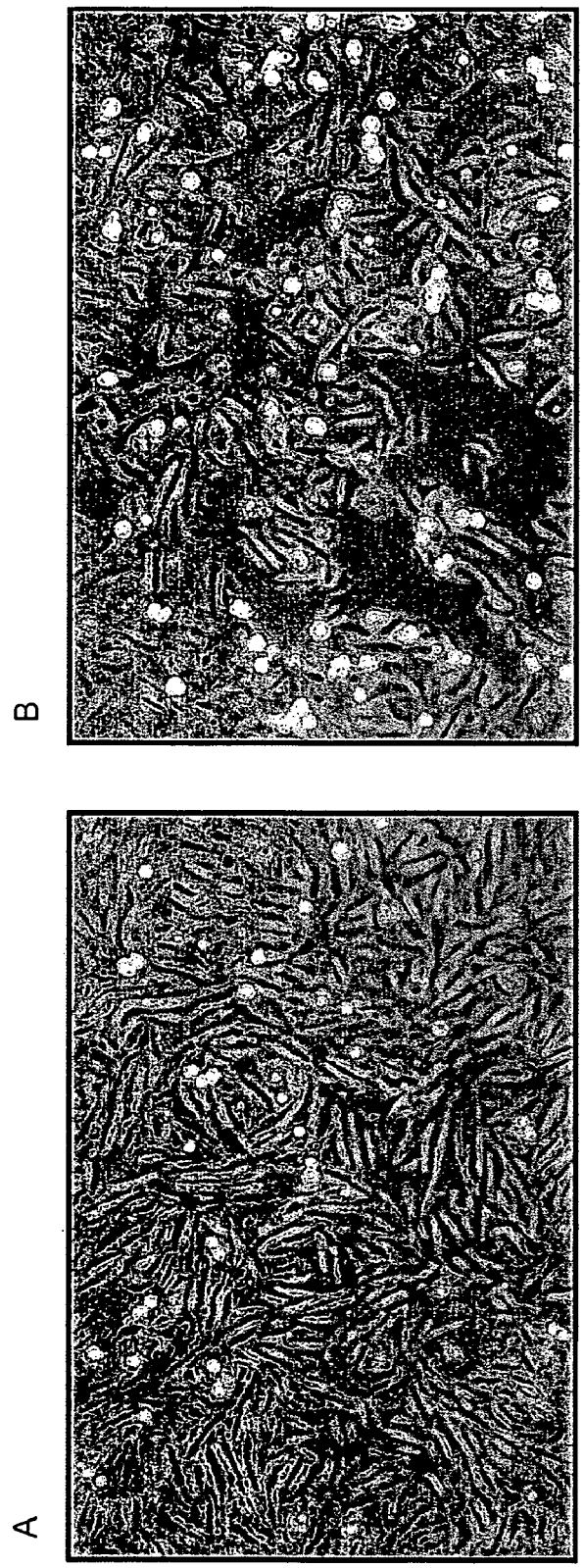
Figure 7:
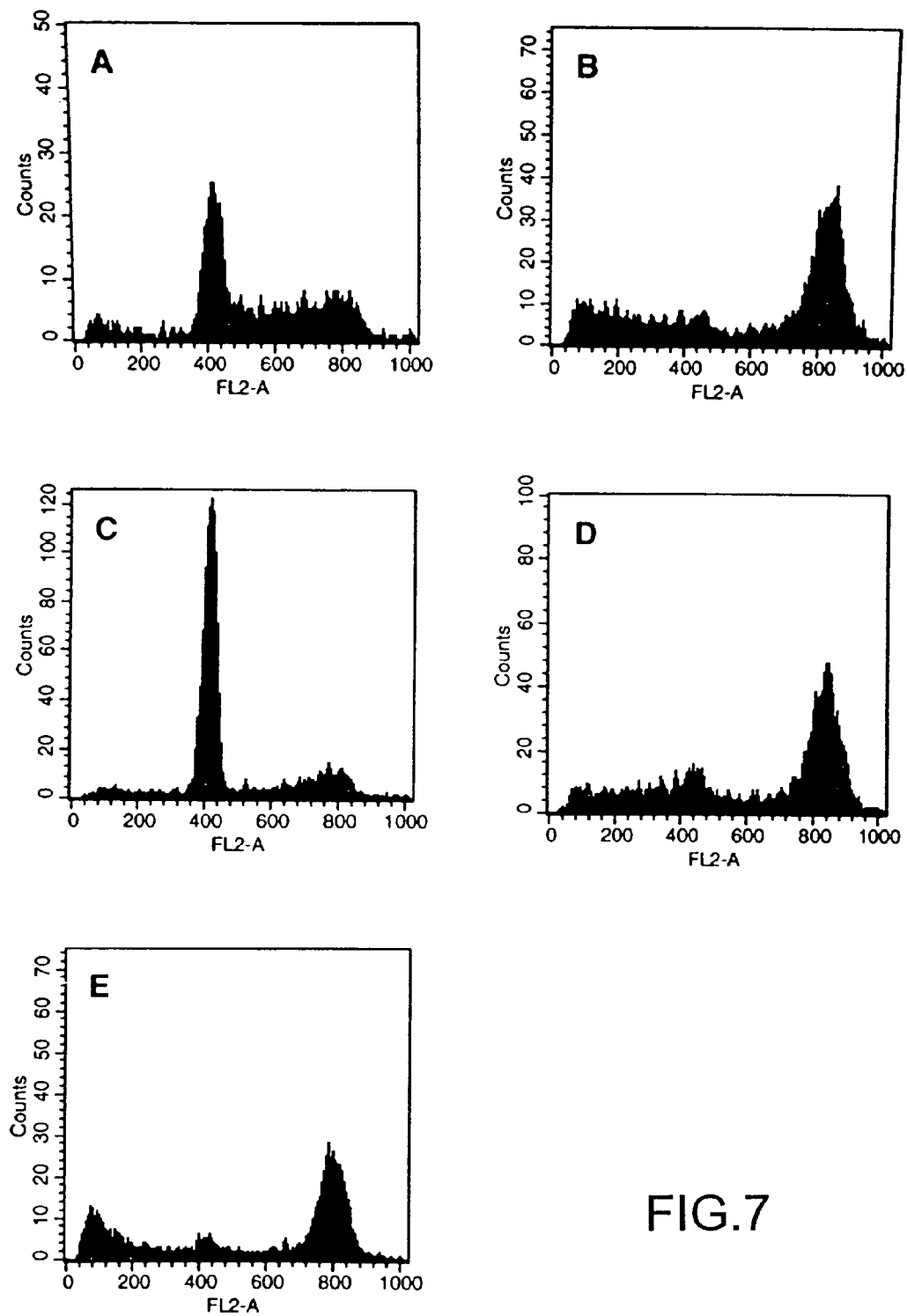
Figure 8:
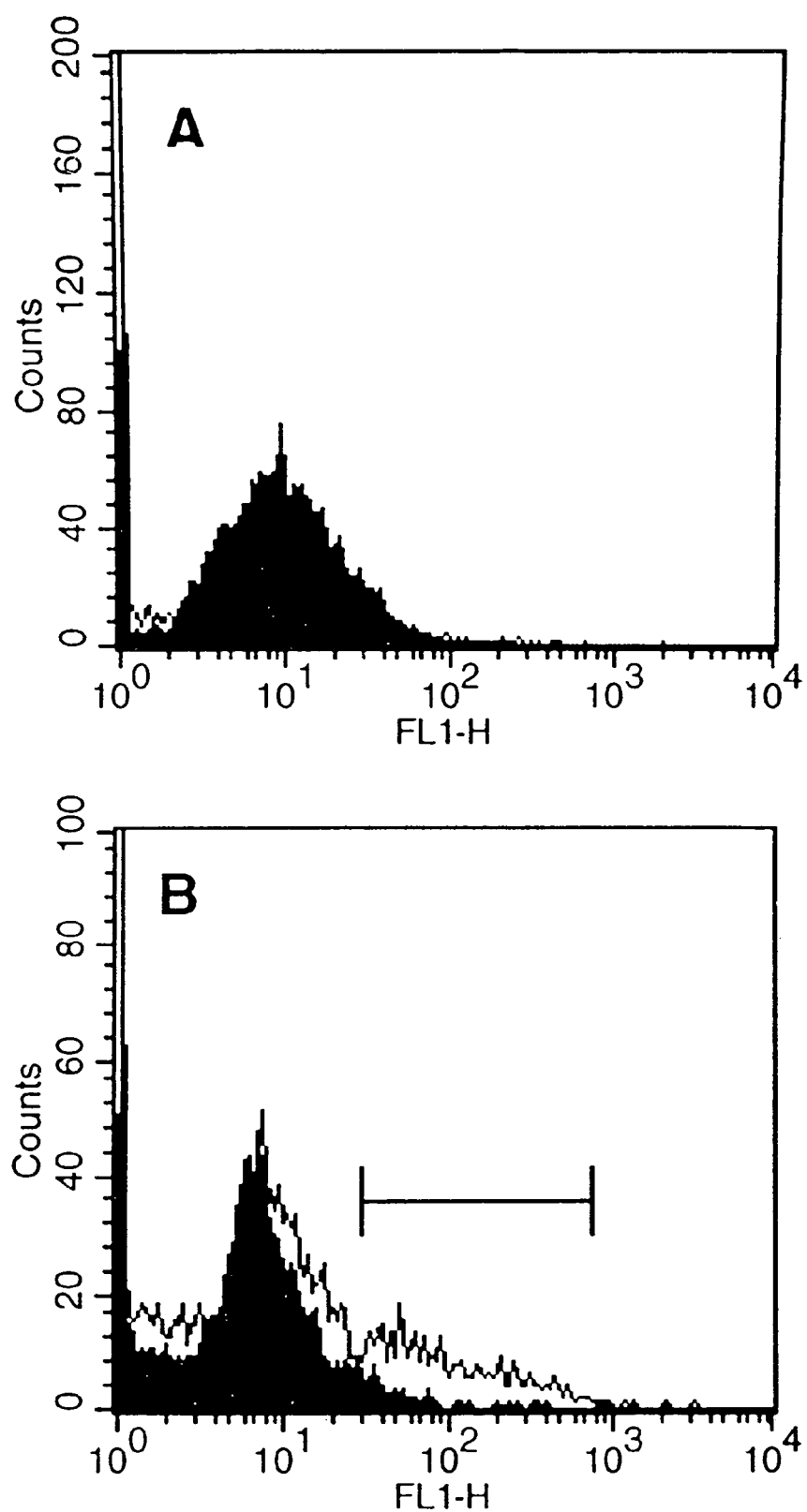
Figure 9:
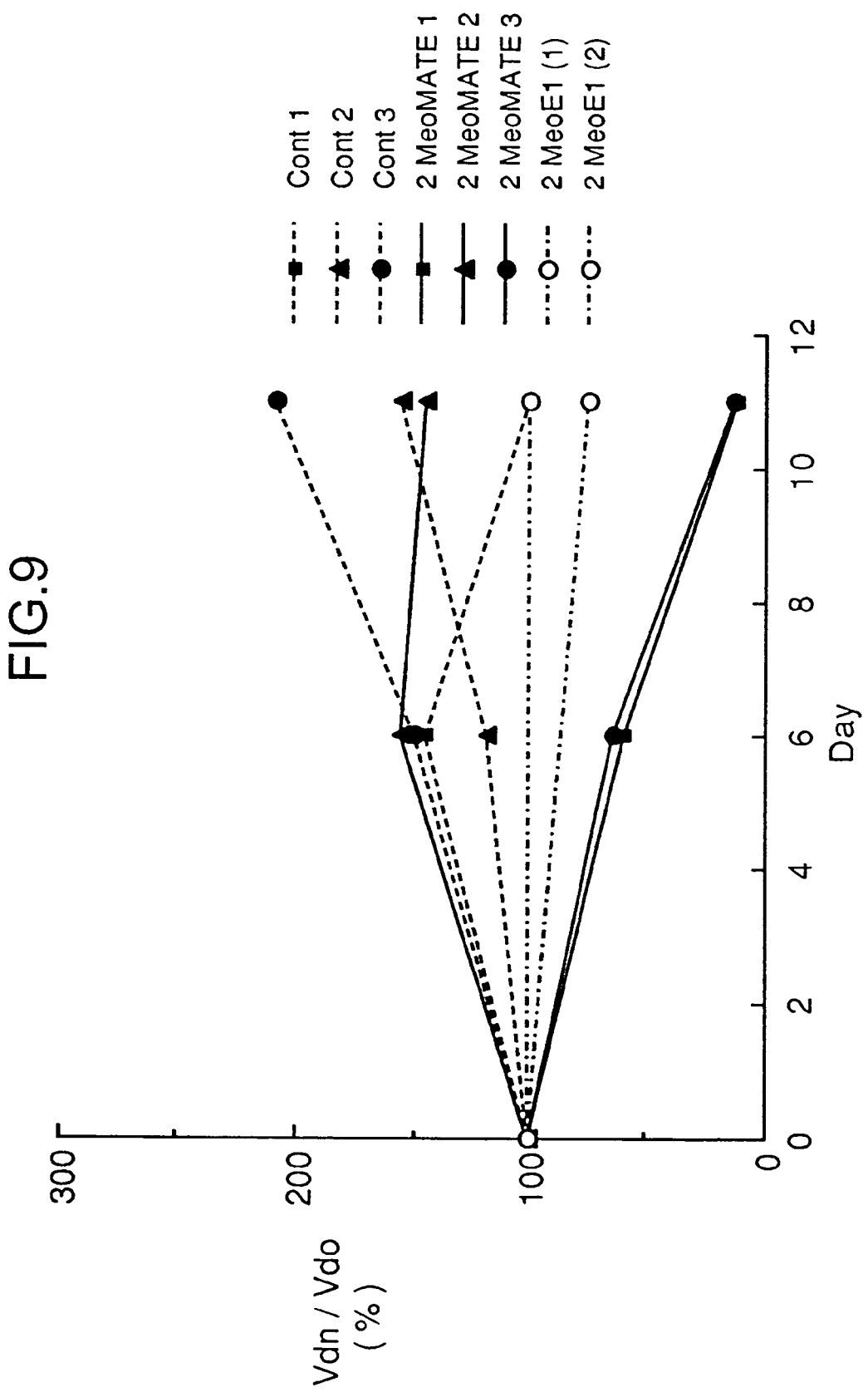
Figure 10:
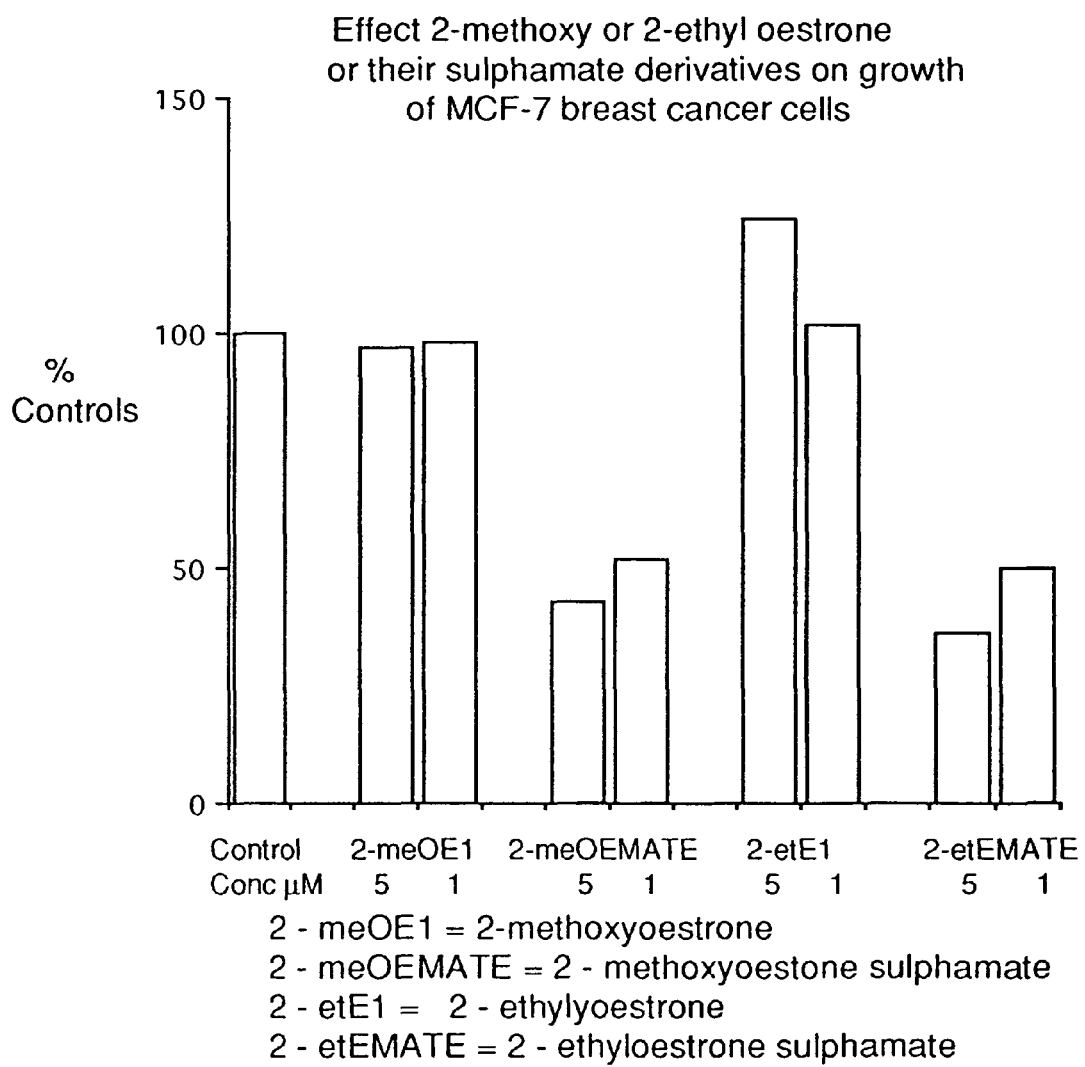
Figure 11:
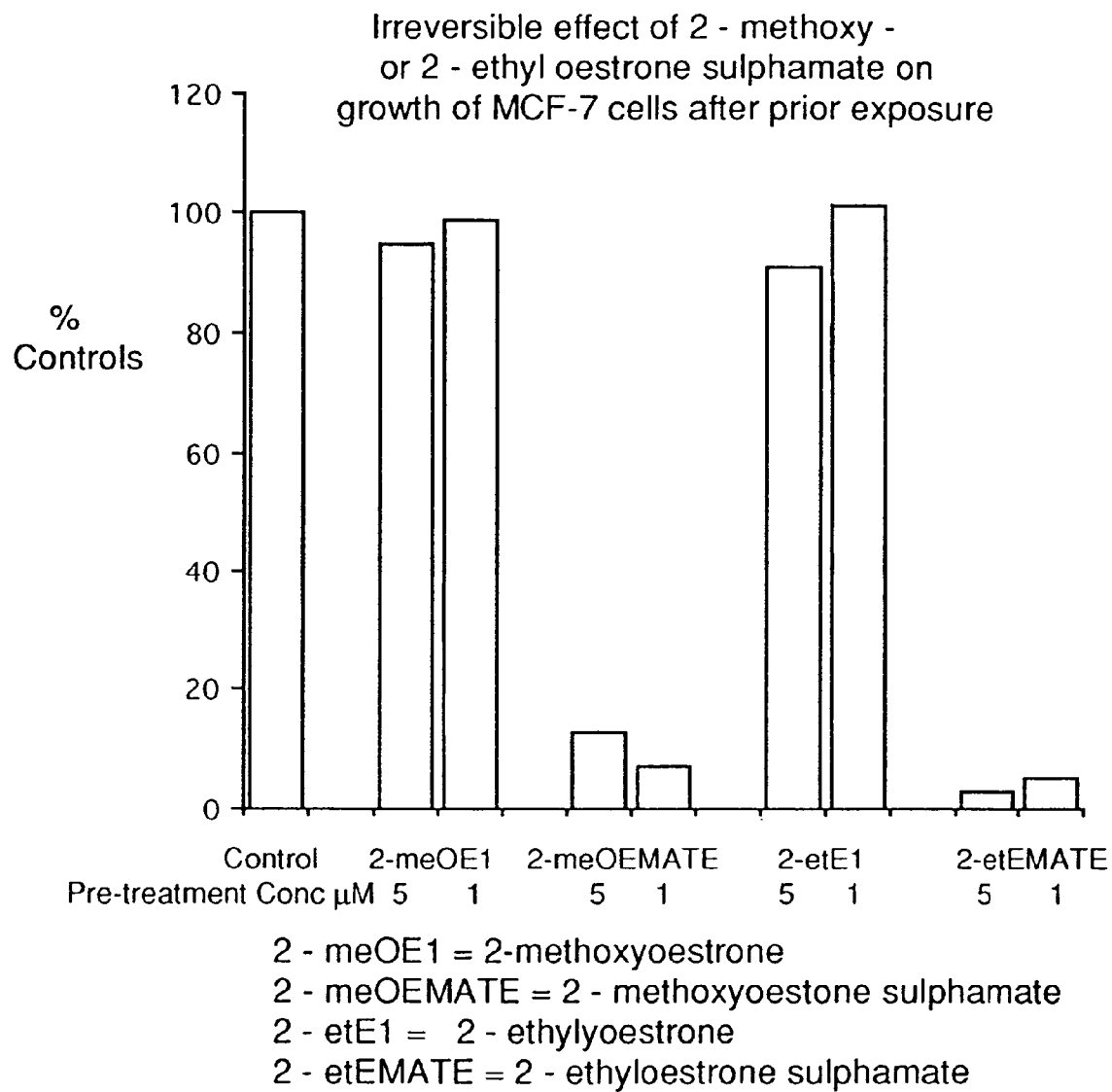
Figure 12:
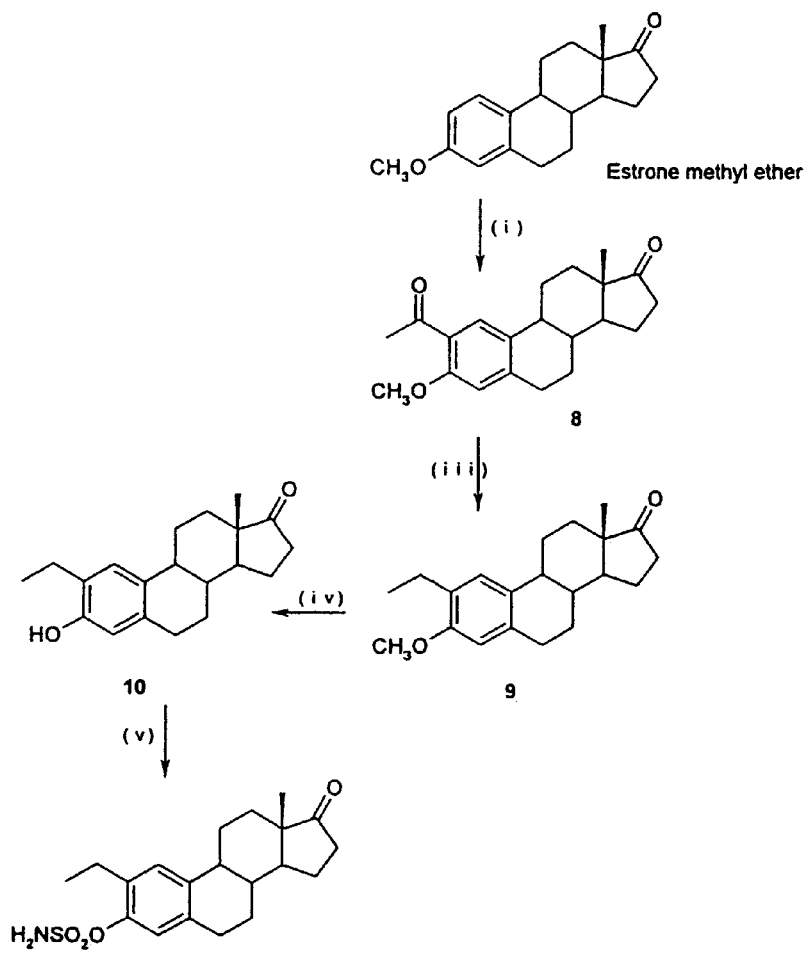
Figure 13:
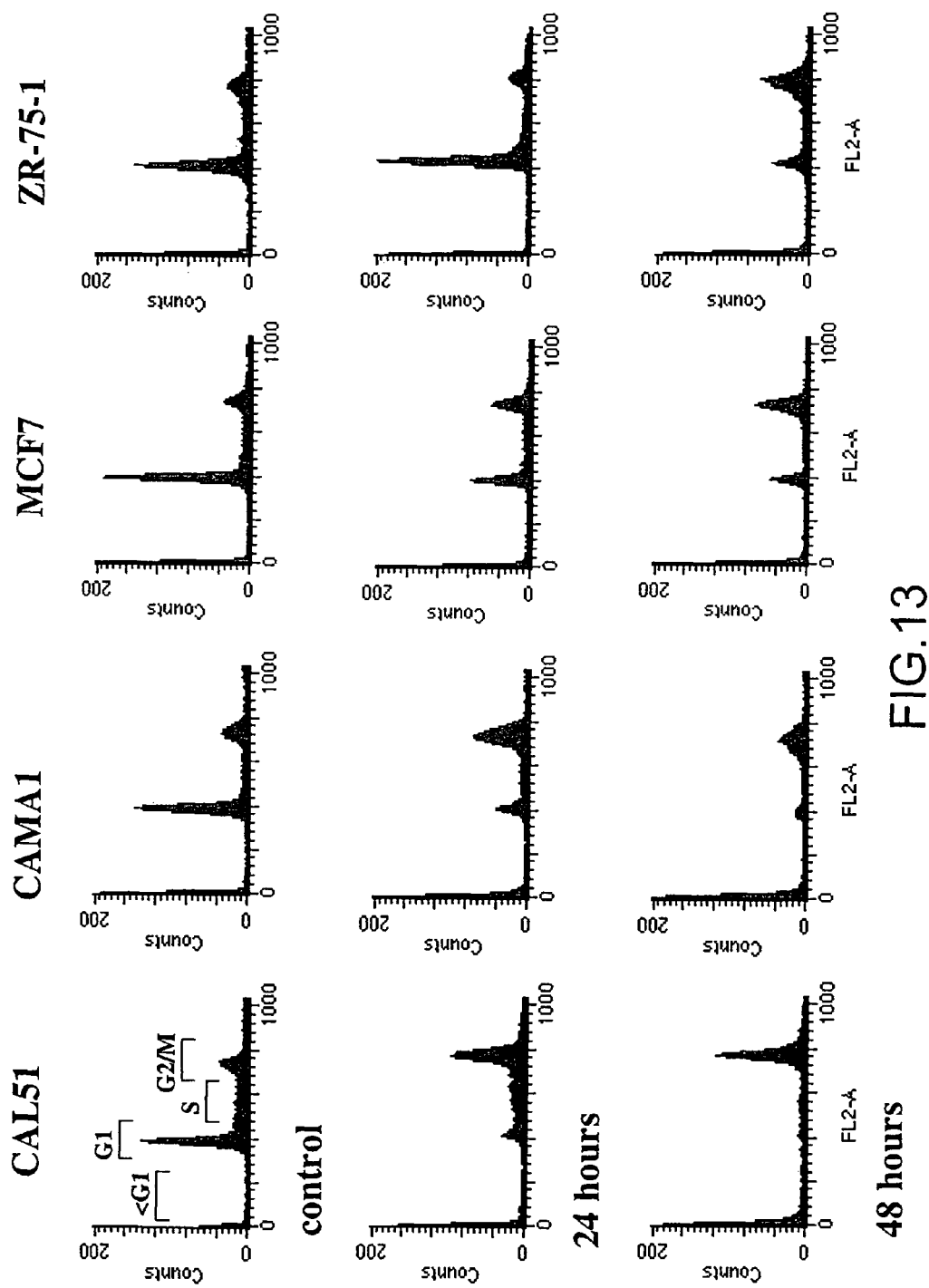
Figure 14:
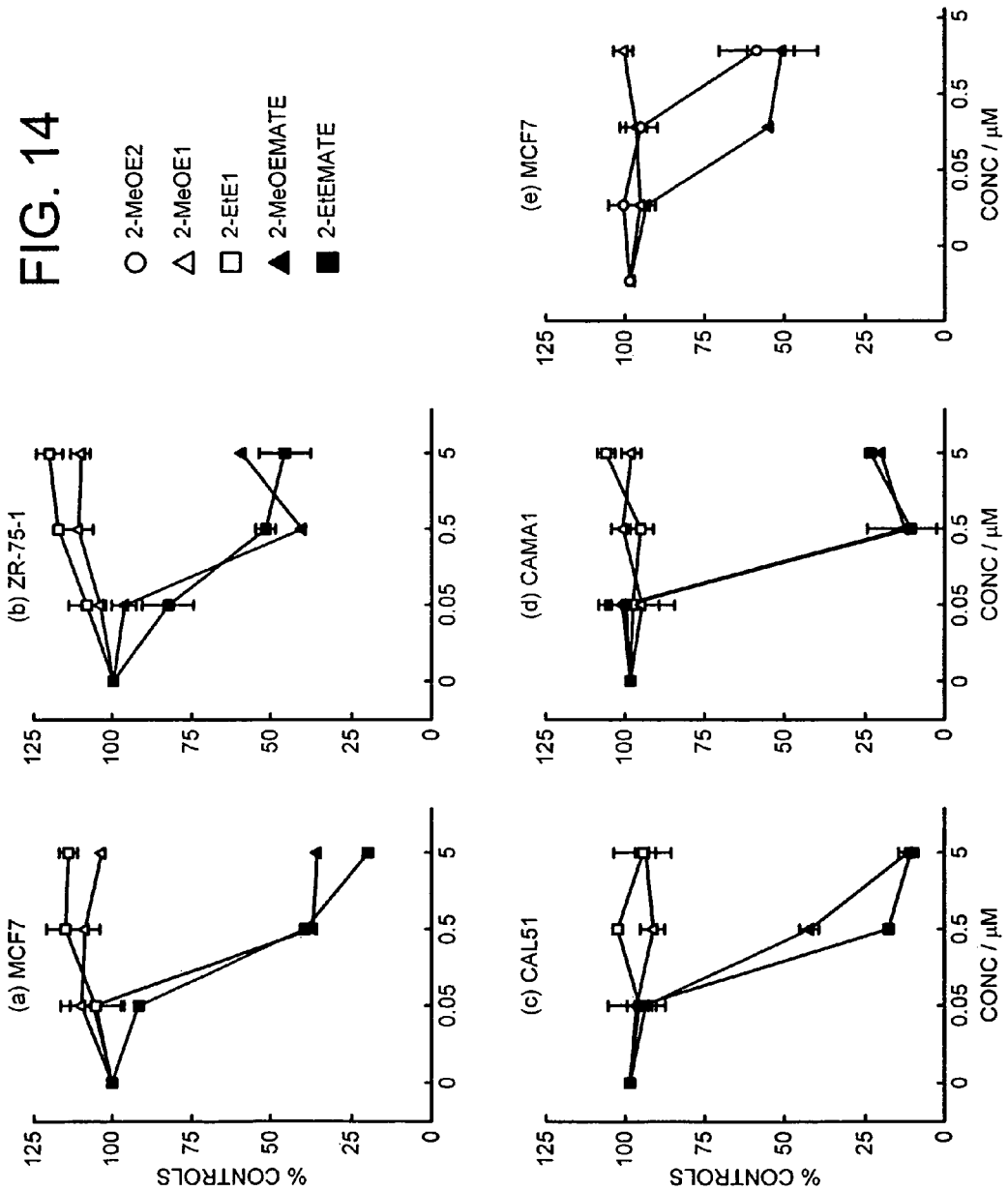
Figure 15:
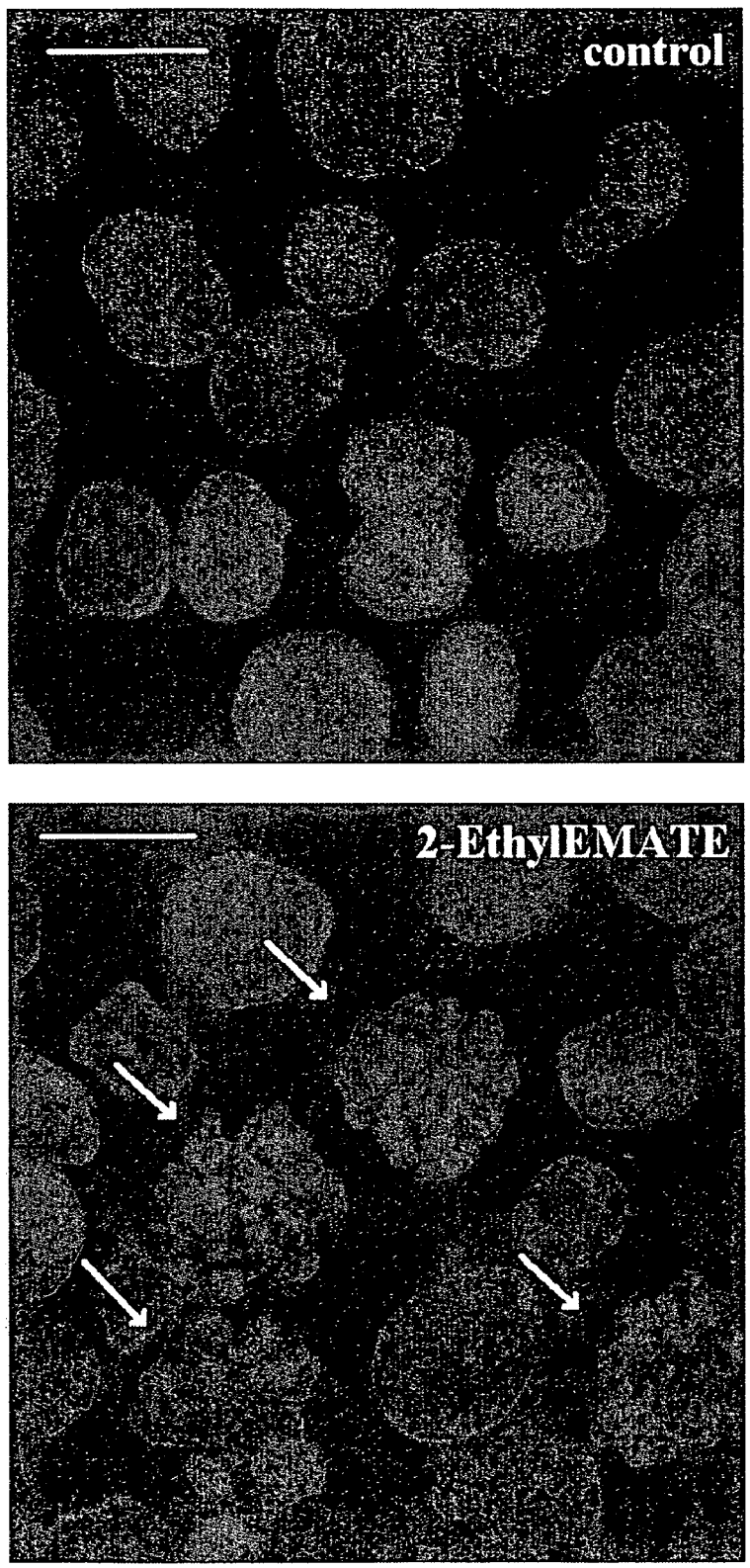

FIG. 1 which illustrates structures;
FIG. 2 which is a graph;
FIG. 3 which is a photographic plate;
FIG. 4 which is a photographic plate
FIG. 5 which is a photographic plate
FIG. 6 which is a graph;
FIG. 7 which is a graph;
FIG. 8 which is a graph;
FIG. 9 which is a graph;
FIG. 10 which is a graph;
FIG. 11 which is a graph;
FIG. 12 which illustrates structures;
FIG. 13 which are graphs;

FIG. 14 which are graphs;

FIG. 15 which is a photographic plate; and

Figure 16:
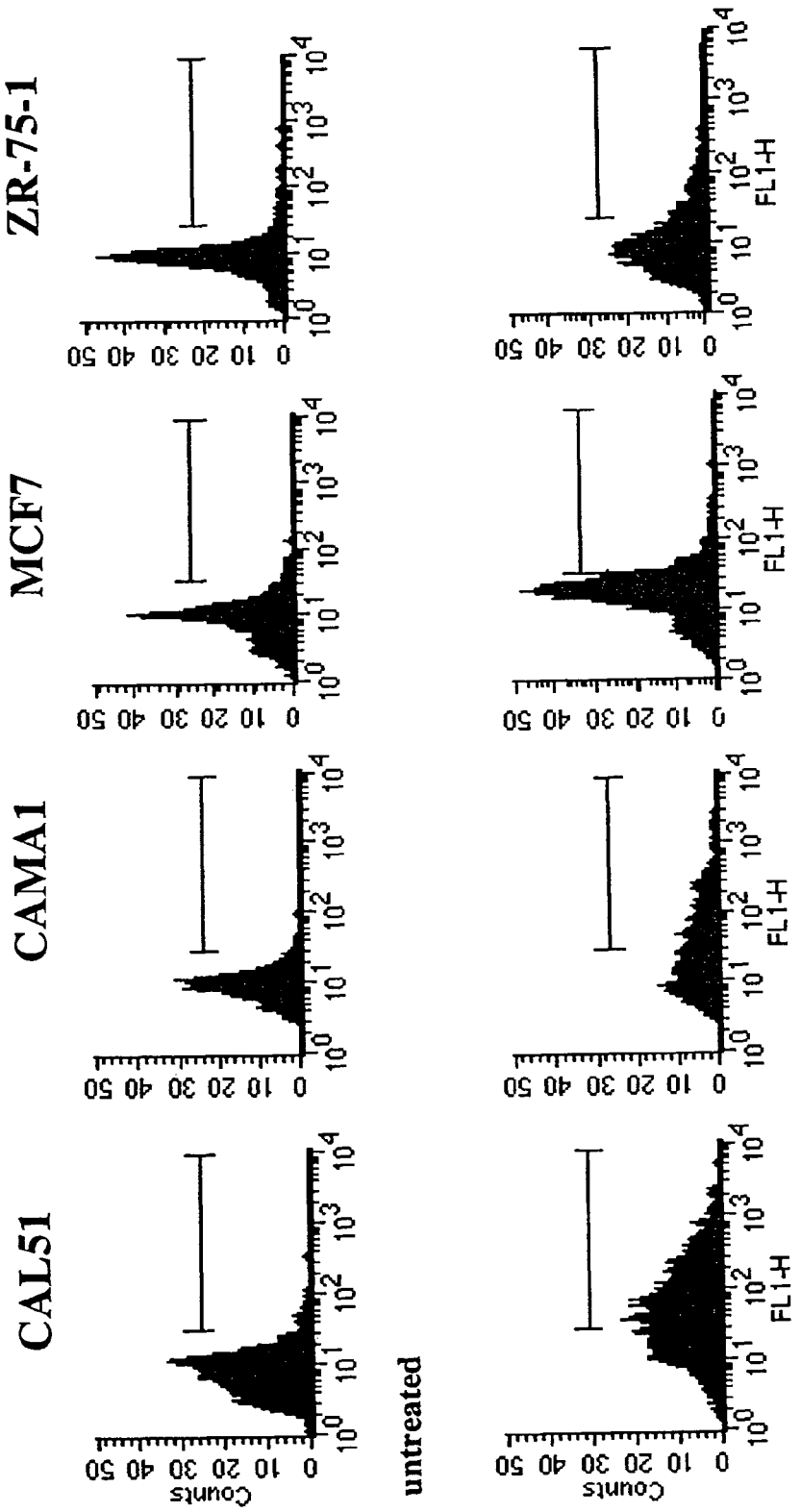

FIG. 16 which are graphs.

FIG. 1 Structures: compound 1, 2-methoxyoestradiol (2-MeOE2); 2, oestrone-3-O-sulphamate (EMATE); 3,2-methoxyoestrone-3-O-sulphamate (2-MeOEMATE); 4,2-methoxyoestrone (2-MeOE1); 5, genistein bis-sulphamate (GenMATE); 6, genistein, 7,2-methoxyoestrone-3-sulphate (2-MeOE1S).

FIG. 2 Dose-response showing the effects of 2-methoxyoestrone (2-MeOE1) or 2-methoxyoestrone-3-O-sulphamate (2-MeOEMATE) on the proliferation of MCF-7 breast cancer cells. Cells (5000 per well) were exposed to drug for 4 days (means±s.d., n=3).

FIG. 3 Effect of a) vehicle, b) 2-methoxyoestrone-3-O-sulphamate (2-MeOEMATE, 1 µM) or 2-methoxyoestrone (2-MeOE1, 1 µM) on MCF-7 breast cancer cells after 24 h.

FIG. 4 Effect of a) vehicle or b) 2-methoxyoestrone-3-O-sulphamate (2-MeOEMATE, 1 µM) on MDA-MB-231 breast cancer cells after 24 h.

Figure 5:
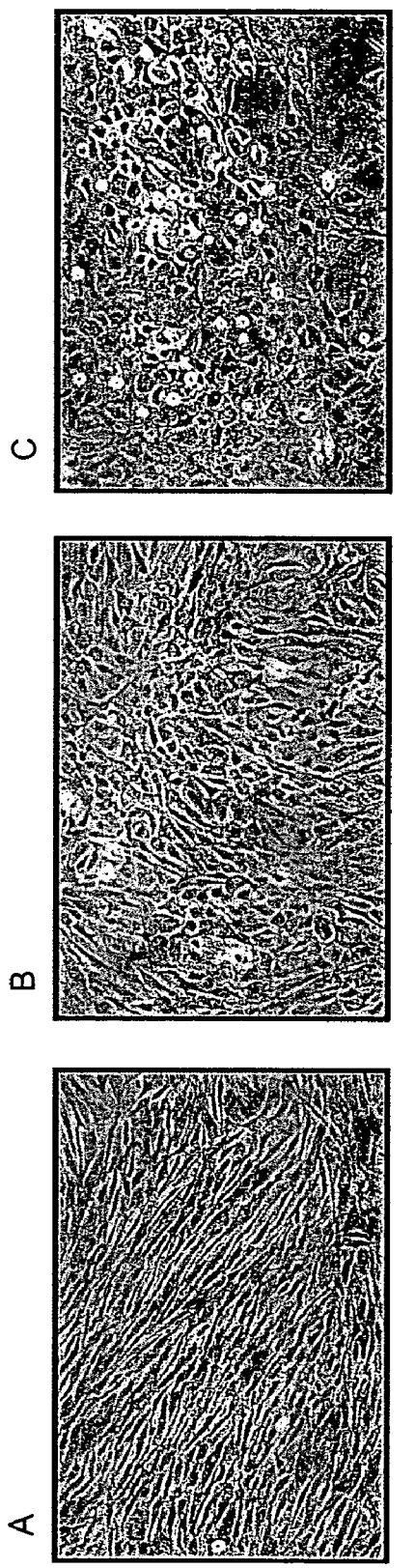

FIG. 5 Effect of a) vehicle, b) 2-methoxyoestrone-3-O-sulphamate (2-MeOEMATE, 1 µM) or c) 2-MeOEMATE (5 µM) on breast tumour-derived fibroblasts at 24 h.

Figure 6:
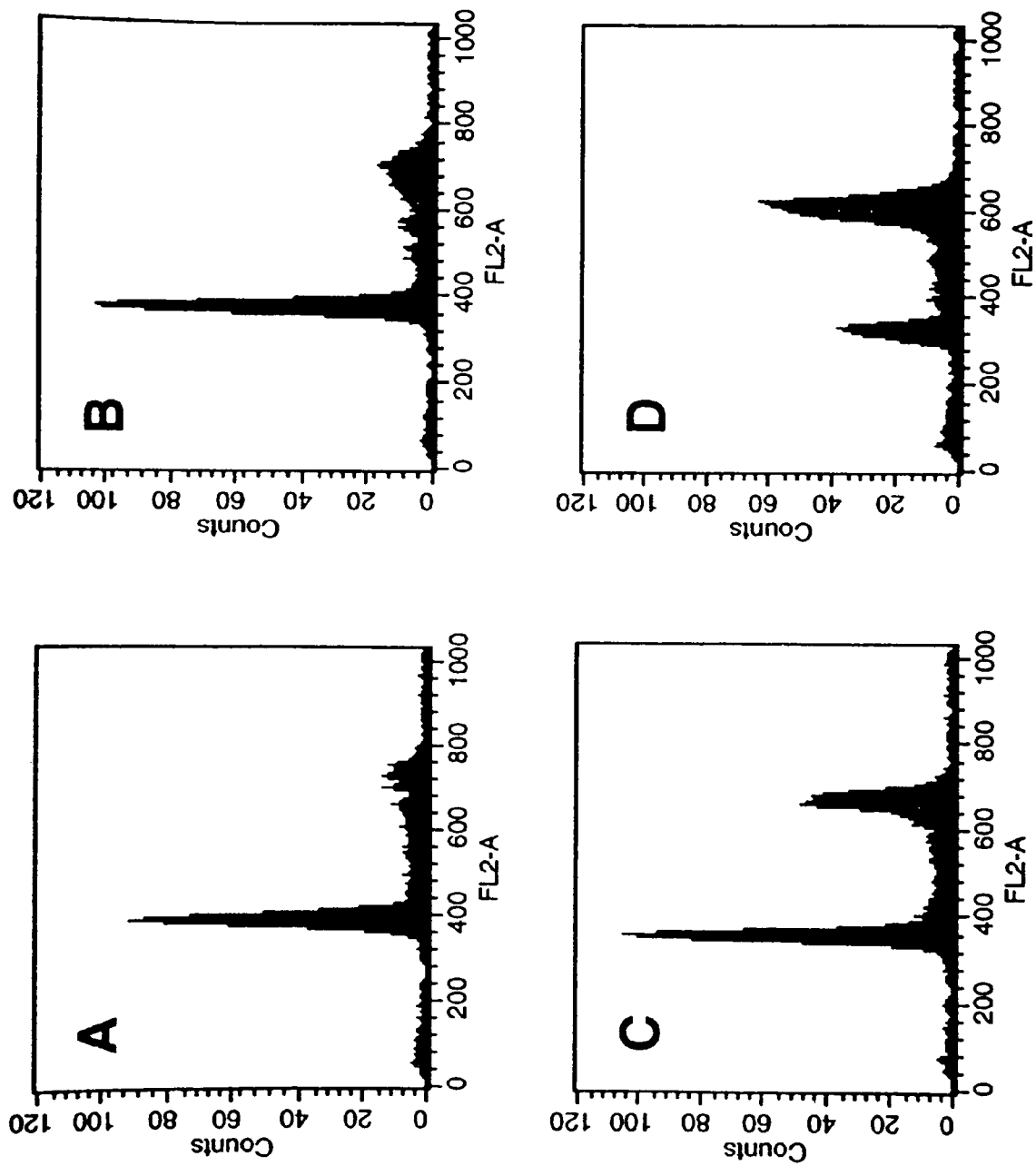

FIG. 6 DNA histograms of vehicle (A) or 2-methoxyoestrone-3-O-sulphamate (10 µM) treated MCF-7 breast cancer cells at 4 h (B), 12 h (C) or 24 h (D). By 12 h after treatment there was evidence of an arrest of cells at the $G_2/M$ phase.

FIG. 7 DNA histogram of 2-methoxyoestrone-3-O-sulphamate (10 µM) treated MCF-7 breast cancer cell s. Compared with controls at 24 h (A) or 48 h (C) cells treated with drug showed a significant increase in the proportion of cells in the $G_2/M$ phase at 24 h (B) and 48 h (D), but also an increase in the sub-$G_1$ fraction. After exposure of cells for 24 h, removal of the drug with a further 24 h culture in drug-free medium did not reverse the arrest of cells in the $G_2/M$ phase (E).

FIG. 8 TUNEL analysis of control MCF-7 cells (A) or cells exposed to 2-methoxyoestrone-3-O-sulphamate (10 µM) for 48 h (B). Histograms are overlays for cells stained in the absence of TdT (bold) or cells stained with TUNEL reaction mixture (open). The bar in the lower figure represents TUNEL positive cells and represents approximately 10% of treated cells.

FIG. 9 Effect of vehicle (propylene glycol, control animals 1-3), 2-methoxyoestrone (2-MeOE1, 20 mg/kg/d, p.o. for 11 days in two animals) or 2-methoxyoestrone-3-O-sulphamate (20 mg/kg/d, p.o. for 11 days in 3 animals) on the growth of nitrosomethylurea-induced mammary tumours in intact rats. Results are expressed as the tumour volumes (expressed as a percentage) on days 6 or 11 (Vdn) compared with their volumes at the start of drug administration.

FIG. 10 Effect of 2-methoxy or 2-ethyl oestrone or their sulphamate derivatives on growth of MCF-7 breast cancer cells.

FIG. 11 Irreversible effect of 2-methoxy or 2-ethyl oestrone sulphamate on growth of MCF-7 breast cancer cells after prior exposure.

FIG. 12 Structures: compound 8, 2-Acetylestrone 3-methyl ether; 9, 2-Ethylestrone 3-methyl ether; 10, 2-Ethylestrone; 11, 2-Ethylestrone 3-O-sulphamate.

FIG. 13 Effects of 2-EtEMATE on the DNA content of MCF7, ZR-75-1, CAL51 and CAMA1 cells using flow cytometry of propidium iodide (PI) stained cells.

FIG. 14 Effects of 2-MeOE2, 2-MeOE1, 2-EtE1, 2-MeOEMATE, and 2-EtEMATE, on MCF7, ZR-75-1, CAL51 and CAMA1.

FIG. 15 Photographic plate of stained nuclei after 2EtEMATE exposure.

FIG. 16 Effects of 2-EtEMATE, on MCF7, ZR-75-1, CAL51 and CAMA1.

General Methods

All reagents and solvents employed were of general purpose or analytical grade unless otherwise stated, and purchased from either Aldrich or Sigma Chemicals or Lancaster Synthesis.

Silica gel refers to silica gel, Merck, grade 60. Product(s) and starting material were detected either viewing under UV light or treating with a methanolic solution of phosphomolybic acid followed by heating. NMR spectra were determined using acetone-$d_6$, CDCl$_3$ or DMSO-$d_6$ as solvent and TMS as internal standard, unless otherwise stated. The $^1$H NMR and $^{13}$C NMR spectra were recorded on a Jeol GX 270 at 270 MHz and on a Jeol EX 400 at 400 MHz NMR spectrometer. The following abbreviations are used to describe resonances in $^1$H NMR and $^{13}$C NMR spectra: s, singlet; d, doublet; br, broad; t, triplet; q, quartet; m, multiplet and combination such as dd, doublet of doublets. IR spectra were determined as KBr discs, using a Perkin-Elmer 782 Infra-Red Spectrophotometer. Melting points were determined on a Reichert-Jung Kofler Block and are uncorrected. Mass spectra were recorded on VG 7070 and VG Autospec instruments at the Mass Spectrometry Service at the University of Bath. FAB-mass spectra were carried out using m-nitrobenzyl alcohol (m-NBA) as the matrix. HPLC stability studies were determined using LDC Constametric 3000 HPLC Pump and Spectrometer 3000 variable wave length detector. CHN analysis was determined using gas chromatography at the Microanalysis Service at the University of Bath.

All reagents and solvents used were stored away from moisture and light and dried before use. Low temperature experiments were conducted using a well insulated external bath containing either ice/water with NaCl for 0° C. or carbon dioxide pellets with acetone or using cold plate. Experiments requiring anhydrous conditions were guarded by mean of a drying tube containing self-indicating silica. Evaporation of solvents was carried out with a rotary evaporator at reduced pressure (water pump) and on stated occasions, followed by the use of a high vacuum pump. Samples were dried in drying tube under high vacuum and low temperature.

All assays were performed at the Department of Endocrinology and Metabolic Medicine, Imperial College School of Medicine, St. Mary's Hospital, London.

Preparation of Sulphamoyl Chloride

Sulphamoyl chloride was prepared by the reaction of chlorosulphonyl isocyanate with formic acid according to the method of Appel and Berger.[44] To anhydrous sulphur-free toluene (150 ml) chlorosulphonyl isocyanate (25 g., 177 mmol) was added at 0° C. under an atmosphere of $N_2$. After stirring, formic acid (6.0 ml, 156 mmol) was added dropwise at 0° C. under $N_2$. The resulting white light emulsion was kept stirring overnight and the toluene removed by using a water vacuum pump to give a light yellow crude of sulphamoyl chloride (16.24 g, 79%). A standard solution (ca 0.70 M) of sulphamoyl chloride was then prepared by dissolving the crude crystalline product in anhydrous sulphur-impurities-free toluene and stored in the refrigerator under $N_2$. No titration was attempted on this sulphamoyl chloride solution whose molarity was estimated according to the weight of the original crude sulphamoyl chloride obtained after workup. Toluene used for preparing sulphamoyl chloride solution was purified according to the method described.[45] Cold toluene (1-3 litres) was placed in a separating funnel and washed with cold conc. $H_2SO_4$ (100 ml/litres, 3-4 times), once with water, once with aqueous 5% NaOH and again with water until neutral, dried with anhydrous MgSO$_4$ followed by sodium metal overnight and then fractionally distilled under N$_2$ from the sodium metal and stored in dark under N$_2$.

Anhydrous formic acid used for preparing sulphamoyl chloride was purified according the method described. Formic acid (98%) was stirred overnight with boric anhydride and then distilled under N$_2$, stored in dark under N$_2$.

General Method for Sulphamoylation

Starting with the parent compound, the sulphamate derivatives were prepared essentially as described by Howarth et al.[14] unless stated otherwise, In this regard, a solution of the appropriate parent compound in anhydrous DMF was treated with sodium hydride [60% dispersion; 1.2 and 2.5 equiv. for monohydroxyl and dihydroxyl compounds respectively, unless stated otherwise] at 0° C. under an atmosphere of N$_2$. After evolution of hydrogen had ceased, sulphamoyl chloride in toluene [excess, ca. 5-6 eq.] was added and the reaction mixture was poured into brine after warming to room temperature overnight and ethyl acetate was added. The organic fraction was washed exhaustively with brine, dried (MgSO$_4$), filtered and evaporated under reduced pressure. The crude product obtained was purified by flash chromatography or preparative TLC followed by recrystallisation to give the corresponding sulphamate. All the compounds were characterised by spectroscopic and combustion analysis.

Synthesis of 2-methoxyoestrone-3-O-sulphamate (2-methoxy EMATE)

2-methoxy EMATE (FIG. 1, 3, 2-MeOEMATE) was synthesised by treating a solution of 2 methoxyoestrone (FIG. 1, 4, 2-MeOE1) in anhydrous dimethylformamide with sodium hydride at 0° C. After evolution of hydrogen had ceased sulphamoyl chloride (2 equiv.) was added and the reaction mixture was allowed to warm to room temperature overnight. The compound was purified by silica gel flash chromatography, was a single pure spot by TLC and exhibited satisfactory spectroscopic and microanalytical data.

In this regard, 2-Methoxy oestrone (75 mg, 0.250 mmol) gave a crude product (103 mg) which was fractionated on silica (50 g) with chloroform/acetone (8:1) and upon evaporation the second fraction gave a pale white residue (83 mg, 81%) which was recrystallised in ethylacetate/hexane (1:2) to give 1 as white crystals (69 mg) .m.p=177-180° C., R$_f$s=0.29 and 0.54 for chloroform/acetone 8:1 and 4:1 respectively and 0.46 and 0.31 for ethylacetate/hexane 2:1 and 1:1 respectively. νmax (KBr) 3400, 3300 (—NH$_2$), 1610 (C=O), and 1380 (—SO$_2$N—) cm$^{-1}$. $\delta_H$ (CDCl$_3$) 0.922 (3H, s, C-18-CH$_3$), 1.24-2.87 (15H, m), 3.88 (3H, s, C-2-OCH$_3$), 5.0 (2H, br s, exchanged with D$_2$O,—SO$_2$NH$_2$), 6.93 (1H, s, C-1-H) and 7.06 (1H, s, C-4-H). MS: m/z (+ve ion FAB in m– NBA, rel. intensity) 379.1 [100, (M)$^+$], 300.0 [25, (M-SO$_2$NH$_2$)$^+$]. MS: m/z (–ve ion FAB in m-NBA, rel. intensity) 378.0 [100, (M–H)$^-$]. Acc. MS: m/z (FAB$^+$)=380.1515 C$_{19}$H$_{26}$NO$_5$S requires 380.1532 Found C, 60.0; H, 6.7; N, 3.67; C$_{19}$H$_{25}$NO$_5$S requires C, 60.14; H, 6.64; N, 3.69%.

Genistein bis-sulphamate (FIG. 1, 5, GenMATE) was prepared from genistein (FIG. 1, 6) by the same procedure with the exception that 2.5 eq sodium hydride was used.

2-Methoxyoestrone and other steroids, cytochalasin B were obtained from Sigma (Poole, Dorset, UK). Genistein for the sulphamoylation reaction was obtained from Lancaster (Manchester UK).

Synthesis of 2-Ethylestrone (2-EtE1) and 2-Ethylestrone-3-O-sulfamate (2-EtEMATE)

2-Ethylestrone (2-EtE1) and 2-Ethylestrone-3-O-sulfamate (2-EtEMATE) were prepared as follows see: briefly, Friedel-Crafts acetylation of estrone-3-O-methyl ether and catalytic hydrogenation followed by demethylation gave 2-Ethylestrone (2-EtE1) which was reacted with sulfamoyl chloride to give the corresponding 3-O-sulfamate (2-EtEMATE). 2-Ethylestradiol has been synthesised previously by a different route (21). Compounds were prepared as 10 mM stocks in tetrahydrofuran (THF).

2-Acetylestrone 3-methyl ether (8)

To a suspension of anhydrous aluminium chloride (3.76 g, 28.20 mmol) and acetyl chloride (2.0 ml, 28.13 mmol) and anhydrous nitromethane/dichloromethane (50 ml) at 0° C., estrone methyl ether (4.0 g, 14.07 mmol) was added. After being stirred for 5 h at room temperature, The reaction mixture was poured into 10% HCl (100 ml) and the resulting mixture was extracted with ethyl acetate (3×100 ml). The combined organic extracts were washed with, brine until neutral, dried (MgSO$_4$), filtered and evaporated. The yellow/brown residue that was obtained was triturated with methanol and the resulting white precipitate was collected by filtration and air-dried to give a white solid (4.3 g) which was recrystallized from methanol to give 8 as white crystals (4.0 g, 87%); mp 181-184° C. (lit. 189-190° C.);[224] TLC (chloroform/acetone, 8:1): Rf 0.82; νmax (KBr) 1730 (C-17, C=O), 1670 (acetyl, C=O) cm$^{-1}$; $\delta_H$ (400 MHz, CDCl$_3$) 0.9 (3H, s, C-18-CH$_3$), 1.39-2.54 (13H, m), 2.61 (3H, s, CH$_3$CO), 2.94 (2H, t, J=4.4 Hz, C-6-H$_2$), 3.88 (3H, s, OCH$_3$), 6.69 (1H, s, C-4-H), and 7.7 (1H, s, C-1-H); $\delta_C$ (400 MHz, CDCl$_3$) 13.83 (q, C-18), 21.56 (t), 25.82 (t), 26.3 (q, CH$_3$CO), 29.9 (t), 31.44 (t), 31.93 (t), 35.84 (t), 38.24 (d), 43.75 (d), 47.95 (s, C13), 50.33 (d), 55.5 (q, OCH$_3$), 111.81 (d, C-4), 127.66 (d, C-1), 125.67 (s) 132.08 (s), 143.21 (s), 157.15 (s, C-3), 199.39 (s, C=O) and 220 (s, C-17-C=O). MS m/z (FAB+) 327.2 [100, (M+H)$^+$], 311.2 (10), 173.2 (5). Found C, 77.4; H, 8.04 C$_{21}$H$_{26}$O$_3$ requires C, 77.27; H, 8.03%.

2-Ethylestrone 3-methyl ether (9)

A solution of 8 (1.0 g, 3.063 mmol) in THF/ethanol (1:2) (30 ml) was hydrogenated in the presence of Pd—C (1.0 g, 10%) 50 psi at room temperature for 24 h. After the supported catalyst was removed by filtration the filtrate was evaporated to give a white solid (950 mg) which was fractionated by flash chromatography (chloroform/acetone gradient). The less polar fraction gave a white solid (805 mg) which was further purified by recrystallization from methanol to give 9 as white crystals (775 mg, 78%); mp 112-115° C.; TLC (chloroform, and chloroform/acetone, 8:1): Rfs 0.56 and 0.78 respectively; νmax (KBr) 1730 (C=O), 1600 cm$^{-1}$; $\delta_H$ ((400 MHz, CDCl$_3$), CDCl$_3$) 0.91 (3H, s, C-18-CH$_3$), 1.17 (3H, t, J=7.7 Hz, CH$_3$CH$_2$), 1.39-2.48 (13H, m), 2.62 (2H, q, C-2-CH$_2$CH$_3$), 2.87 (2H, m, C-6-H$_2$), 3.81 (3H, s, OCH$_3$), 6.58 (1H, s, C-4-H), and 7.08 (1H, s, C-1-H); $\delta_C$ (400 MHz, CDCl$_3$) 13.86 (q), 14.54 (q), 21.58 (t), 22.86 (t), 25.82 (t), 26.17 (t), 29.72 (t), 31.63 (t), 35.88 (t), 38.23 (d), 44.04 (d), 48.23 (s, C13), 50.38, 55.32 (q, OCH$_3$), 110.8 (d, C-4), 126.34 (d, C-1), 130.08 (s), 131.31 (s), 134.71 (d), 155.41 (s) and 220 (C-17, C=O); MS m/z (FAB+) 312.1 [100, (M)$^+$]. Found C, 80.5; H, 9.03 C$_{21}$H$_{28}$O$_2$ requires C, 80.73; H, 9.03%.

2-Ethylestrone (10)

Aluminum chloride (1.28 g, 9.615 mmol), sodium iodide (1.44 g, 9.615 mmol) and 9 (300 mg, 961.5 μmol) were added in this order to a mixture of acetonitrile (25 ml) and dichloromethane (12.5 ml) at 0° C. under N$_2$. The resulting suspension was heated under reflux for 8 h, cooled to room temperature and then poured into water and followed by extraction with dichloromethane (3×100 ml). The combined DCM extracts were washed with 10% sodium thiosulphate (100 ml), brine, dried (MgSO$_4$), filtered and evaporated to give a yellow solid (290 mg), which was fractionated by flash chromatography (chloroform/acetone gradient). The yellow solid that isolated (254 mg) was further purified by recrystallization from acetone to give 10 as yellow crystals (240 mg, 83%); mp 201-204° C.; TLC (chloroform and chloroform/acetone, 8:1): Rf 0.3 and 0.65 respectively; vmax (KBr) 3300 (OH), 1720 (C=O) cm$^{-1}$; $\delta_H$ (400 MHz, CDCl$_3$) 0.91 (3H, s, C-18-CH$_3$), 1.22 (3H, t, CH$_3$CH$_2$_), 1.38-2.51 (13H, m), 2.63 (2H, q, C-2-CH$_2$ CH$_3$), 2.86 (2H, m, C-6-H$_2$), 4.68 (1H, br s, exchanged with D$_2$O, OH), 6.52 (1H, s, C-4-H) and (1H, s, C-1-H); MS m/z (FAB+) 298.0 [100, (M)$^+$], 271.9 (10), 255.1 (10); MS m/z (FAB−) 297.1 [100, (M−H)$^-$], 276.0 (45), 258.0 (40); Acc. mass (FAB+) 298.1928 requires C$_{20}$H$_{26}$O$_2$ 298.1933.

2-Ethylestrone 3-O-sulphamate (11)

To a stirred solution of 10 (150 mg, 502.6 μmol) and 2,6-di-t-butyl-4-methylpyridine (DBMP) (310 mg, 1.51 mmol) in CH$_2$Cl$_2$ (10 ml), sulphamoyl chloride in toluene (3.016 mmol) was added dropwise. After being stirred for 2 h the reaction mixture was diluted with dichloromethane (100 ml) and the resulting mixture washed with brine, dried (MgSO$_4$), filtered and evaporated. The residue that was obtained (170 mg) was fractionated by flash chromatography (chloroform/acetone gradient) and the white solid that isolated (155 mg) was further purified by recrystallization from ethyl acetate/hexane (1:2) to give 11 as white crystals (146 mg, 77%); mp 165-167° C.; TLC (chloroform/acetone, 8:1): Rf 0.41; vmax (KBr) 3500-3300 (NH$_2$), 1720 (C=O), 1390 (SO$_2$N) cm$^{-1}$; $\delta_H$ (400 MHz, CDCl$_3$) 0.91 (3H, s, C-18-CH$_3$), 1.22 (3H, t, CH$_3$CH$_2$-), 1.41-2.55 (13H, m), 2.71 (2H, q, C-2-CH$_2$CH$_3$), 2.89 (2H, m, C-6-H$_2$), 5.0 (2H, br s, exchanged with D$_2$O, OSO$_2$NH$_2$), 7.11 (1H, s, C-4-H) and 7.2 (1H, s, C-1-H); MS m/z (FAB+) 531.2 [10, (M+H+NBA)$^+$], 377.1 [100, (M)$^+$], 298.2 [20, (M+H—SO$_2$NH$_2$)$^+$]; MS m/z (FAB−) 530.1 [30, (M+NBA)$^-$], 376.1 [100, (M−H)$^-$], 275.1 (10); Acc. MS (FAB+) 377.1683 requires C$_{20}$H$_{27}$NO$_4$S 377.1661. Found C, 63.4; H, 3.73; N, 7.4 requires C$_{20}$H$_{27}$NO$_4$S C, 63.63; H, 3.71; N, 7.21%.

EXAMPLE 1

Cell Culture

MCF-7 (ER+) and MDA-MB-231 (ER−) breast cancer cells were obtained from the American Type Culture Collection (Rockville, Md.). Cells were routinely cultured in 25 cm$^2$ culture flasks in Eagle's minimum essential medium (EMEM) with Hepes buffer (20 mM). This medium was supplemented with L-glutamine (2 mM), sodium hydrogen carbonate (10 mM), 1% non-essential amino acids and 5% (v/v) foetal calf serum (FCS). Before adding test compounds, cells were washed with phosphate-buffered saline (PBS) and treatments added in phenol-red free medium containing 2% stripped FCS and supplements. The effects of 2-MeOE1 or 2-MeOEMATE on the growth of MCF-7 cells was assessed using a Cell Titer 96 cell proliferation assay (Promega, Southampton, Hants, UK) according to the manufacturers' instructions. For this, cells (5000 per well) were cultured in medium containing phenol-red and 10% FCS and were exposed to a drug for 4 days before the assay was performed. For MDA-MB-231 cells, cell numbers were determined using a Coulter counter.

For the culture of fibroblasts, resected breast tumour tissue was minced and incubated in EMEM for 18-24 h at 37° C. with collagenase (200 μg/ml). The dispersed cells were harvested by centrifugation and washed twice with medium to remove collagenase. Dispersed cells were seeded into culture flasks and grown to confluence before passaging on a weekly basis. For experimental purposes 12 well multi-well plates or 25 cm$^2$ flasks were seeded with fibroblasts and grown to 70-80% confluency. Cells were washed with PBS and exposed to drugs for 24 h before determining cell numbers using a Coulter counter.

Photomicrographs of control and treated cells were taken under normal conditions of light and exposure using an Olympus SL35 Type 12 camera under an Olympus CK2 microscope (×100 magnification).

Results

The effect of 2-MeOE1 or 2-MeOEMATE on the proliferation of MCF-7 cells over a 4-day period was determined using a microwell plate proliferation assay (FIG. 2). 2-MeOE1 at 0.1 μM or 1.0 μM had little effect on the proliferation of MCF-7 cells but reduced growth by 19% at 10 μM. In contrast, 2-MeOEMATE inhibited cell proliferation by 29% and 52% respectively at 0.1 μM and 1.0 μM. However, no further effect on cell proliferation was detected when cells were exposed to a higher (10 μM) concentration of 2-MeOEMATE.

Exposure of MCF-7 cells to 2-MeOEMATE had a marked effect on cell morphology (FIG. 3). In untreated cells (FIG. 3a) only a few rounded cells were visible per field, whereas for cells treated with 2-MeOEMATE (1 μM) for 24 h there was a significant increase in the number of rounded and detached cells (FIG. 3b). In contrast, 2-MeOE1 (1 μM) had little effect on cell morphology (FIG. 3c). Oestrone or EMATE when tested at 10 μM did not affect cell morphology (data not shown).

2-MeOEMATE (1 μM) had a similar effect on ER negative MDA-MB-231I breast cancer cell morphology and number (FIGS. 4a and 4b). At 1 μM the number of MDA-MB-231 cells was reduced by 21% compared with untreated cells. As the stromal compartment constitutes a major proportion of the volume of breast tumours the effect of 2-MeOEMATE on the morphology of breast tumour-derived fibroblasts was also examined (FIG. 5). At 1 μM little effect on cell morphology was detected (FIG. 5b) whereas at 5 μM rounding of a significant proportion of fibroblasts occurred (FIG. 5c). In contrast to the effect of 2-MeOEMATE on epithelial cell numbers it did not reduce the number of fibroblasts.

EXAMPLE 2

Flow Cytometry Analysis

Cells were cultured in the presence of 2-MeOE1, 2-MeOEMATE or vehicle for up to 48 h. To examine the reversibility of the effects of 2-MeOEMATE on the cell cycle, cells were treated for 24 h with the drug after which cells were washed and cultured in fresh medium without drug for a further 24 h period.

To prepare cells for analysis of DNA content, cells were trypsinised (0.25% trypsin, 0.02% EDTA), washed with PBS and fixed with 70% ethanol. Cells were collected by centrifugation, re-suspended in PBS (1-2×10$^6$ cells/ml) and treated with RNase A (0.1 mg/ml) and stained with propidium iodide (0.05 mg/ml) for 30 min at room temperature. Cells were analysed with a flow cytometer (FACscan, Becton Dickinson Immunocytometry System, Bedford Mass.).

Results

MCF-7 cells were treated with 2-MeOEMATE (10 μM) and the cell cycle distribution was analysed by flow cytometry. A time-course study revealed a progressive accumulation of cells in the $G_2/M$ phase and the effect was apparent by 12 h after treatment (FIG. 6).

The proportion of cells in the $G_1$ phase of the cell cycle decreased from 66% for untreated cells to 50% and 23% respectively after 12 h or 24 h exposure to 2-MeOEMATE. There were corresponding increases in the proportions of cells in the $G_2/M$ phase with little change in cells in the S phase being detected.

In a reversibility study, MCF-7 cells exposed to 2-MeOEMATE (10 μM) for 24 h or 48 h again showed a marked increase in the proportion of cells in the $G_2/M$ phase of the cell cycle (FIGS. 7a-d). For cells exposed to drug for 24 h after which drug was removed and cells cultured in drug-free medium for a further 24 h, a significant proportion of cells remained arrested in the $G_2/M$ phase (FIG. 7e). Quantitation of cells in the sub-$G_1$, $G_1$, S or $G_2/M$ phase of the cycle (Table 1) confirmed the reciprocal decrease in the proportion of cells in the $G_1$ phase and increase in the $G_2/M$ phase. However, a significant increase in the proportion of cells in the sub-$G_1$ fraction was also detected. Cells in the sub-$G_1$ fraction may represent cells undergoing apoptosis.

TABLE 1

Effect of 2-MeOEMATE (10 μM) on cell cycle distribution

|  | Sub-$G_1$ | $G_1$ | S | $G_2/M$ |
|---|---|---|---|---|
| Control 24 h | 9 | 51 | 21 | 19 |
| 2-MeOEMATE 24 h | 22 | 10 | 8 | 60 |
| 2-MeOEMATE 24 h + 24 h drug-free culture | 27 | 8 | 7 | 57 |
| Control 48 h | 4 | 76 | 8 | 12 |
| 2-MeOEMATE 48 h | 18 | 14 | 9 | 58 |

EXAMPLE 3

TUNEL Analysis

The ability of 2-MeOEMATE to induce apoptosis in MCF-7 cells was examined by TUNEL analysis using an in situ cell death detection kit (Boehringer Manheim UK Ltd., Lewes, East Sussex, UK). Cells were fixed and permeabilised according to the manufacturers' instructions. Stained apoptotic cells were quantitated by flow cytometry.

Results

The possibility that cells in the sub-$G_1$ fraction may represent cells undergoing apoptosis was confirmed in a further experiment by TUNEL analysis (FIG. 8). For untreated cells no increase in the proportion of fluorescently labelled cells was detected after staining. In contrast, there was a significant increase in the proportion of fluorescently labelled cells after exposure to 2-MeOEMATE (10 μM) for 48 h. Fluorescently labelled cells represented approximately 10% of the cell population. This result indicates that 2-MeOEMATE can induce cells to undergo apoptosis.

EXAMPLE 4

Effect of 2-MeOEMATE on Growth of NMU-Induced Mammary Tumours in Intact Rats

The effect of 2-MeOEMATE on mammary tumour growth was examined in a preliminary study using Ludwig rats (Harlan Olac, Bicester, UK) in which tumours were induced by inoculation of NMU. Tumour development was monitored regularly and when 0.5-1.0 cm³ in volume, animals received vehicle (propylene glycol, 200 μl/day, p.o.), 2-MeOEMATE (20 mg/kg/day, p.o.) or 2-MeOE1 (20 mg/kg/day, p.o.) daily for an 11 day period. Tumour length and width was measured with callipers and tumour volumes calculated as described (21).

Results

A preliminary study was carried out to compare the abilities of 2-MeOE1 and 2-MeOEMATE to inhibit tumour growth in vivo. For this, the growth of mammary tumours was initiated by inoculation with NMU. Drugs were administered orally when tumour volumes reached 0.5-1.0 cm³. For two of the animals receiving vehicle, tumour volumes continued to increase (average 82%) while little change in the volume of a tumour in a third animal was detected (FIG. 9). For two animals receiving 2-MeOE1 no change in tumour volume occurred in one, while for the other a modest (25%) reduction was detected over the 11-day period of the study.

For three animals receiving 2-MeOEMATE the tumour volume in one animal continued to increase up to day 6, but thereafter showed a slight (8%) reduction. In contrast, for the two other animals receiving 2-MeOEMATE, tumours regressed rapidly and were barely palpable at the end of the 11-day period. Tumour volumes in the two animals receiving 2-MeOEMATE that regressed were monitored for a further 33 days during which time no regrowth of tumours was detected.

EXAMPLE 5

Irreversible Effect of 2-Methoxy- or 2-Ethyloestrone Sulphamates on Growth of MCF-7 Breast Cancer Cells Procedure Stage 1

MCF-7 breast cancer cells were seeded into multi-well culture plates at a density of $10^5$ cells/well. Cells were allowed to attach and grown until about 30% confluent when they were treated as follows:

Control—no treatment
2-MeOE1 5 μm
2-MeOE1 1 μm
2-MeOEMATE 5 μm
2-MeOEMATE 1 μm
2-EtE1 5 μm
2-EtE1 1 μm
2-EtEMATE 5 μm
2-EtEMATE 1 μm Cells were grown for 6 days in growth medium containing the above drugs with changes of medium/drug every 3 days. At the end of this period cell numbers were counted using a Coulter cell counter.

The results from this first stage of the experiment are shown in FIG. 10. Compared with the controls, 2-methoxyoestrone or 2-ethyloestrone had little effect on cell growth. In contrast, treatment of cells with 2-methoxyoestrone sulphamate at 5 μm or 1 μm reduced cell numbers to 43% and 52% of the control cell number respectively. The corresponding values after treatment of cells with 2-ethyloestrone sulphamate were 36% and 50% respectively.

Stage 2

After treatment of cells for a 6-day period with the above drugs cells were re-seeded at a density of $10^4$ Cells/well. No further treatments were added. Cells were allowed to continue to grow for a further 6 days in the presence of growth medium. At the end of this period cell numbers were again counted.

Results from this part of the experiment are shown in FIG. 11. Compared with the controls 2-methoxyoestrone or 2-ethyloestrone had little effect on cell numbers showing that these compounds have no irreversible growth inhibitory effects on these cells.

In contrast, cells treated with either 2-methoxyoestrone sulphamate or 2-ethyloestrone sulphamate were severely growth restricted. These results demonstrated that once cells have been exposed to 2-methoxyoestrone sulphamate or 2-ethyloestrone sulphamate their growth is irreversibly compromised.

EXAMPLE 6

Effect of Non-Hydrocarbyl/Oxyhydrocarbyl Substituted Sulphamates on Growth of MCF-7 Breast Cancer Cells Procedure Stages 1 and 2 described above were repeated using Control—no treatment, EMATE 20 µM and EMATE 5 µM.

The stage 1 and 2 results were:
Stage 1 EMATE 20 µM=119% control
EMATE 5 µM=139% control
Stage 2 EMATE 20 µM=103% control
EMATE 5 µM=98% control These data show the importance of the hydrocarbyl/oxyhydrocarbyl substituents on the compounds of the present invention to achieve inhibition and/or prevention and/or arrest of cell cycling.

EXAMPLE 7

Cell Cycle and Apoptosis Analysis

MCF7, CAL51, CAMA1 and ZR-75-1 breast cancer derived cell lines were obtained from ATCC (MCF7, CAMA1, ZR-75-1) or from the Dutrillaux laboratory (CAL51) (22) and maintained in Dulbecco's modified Eagle's medium (DMEM) supplemented with 10% (v/v) fetal calf serum and antibiotics.

DNA content was determined by flow cytometric analysis of propidium iodide stained cells and TdT-mediated dUTP-nick end labelling (TUNEL), respectively, as described (20). The proportion of cells in G2/M phase of the cell cycle was calculated as a proportion of cells with 2N to 4N DNA content. The proportion of cells with <G1 DNA content was calculated as a percentage of total cells.

To determine the proportion of cells in mitosis, drug treated cells were collected by trypsinisation and cytospins prepared. Cells were fixed in ice cold methanol for 5 minutes, air dried and DNA was stained using propidium iodide (PI) (0.1 mg/ml in phosphate buffered saline (PBS) containing 10% (v/v) newborn calf serum and 0.05% (w/v) sodium azide). Cells were analysed by confocal microscopy using a Zeiss Axiovert 100 M microscope equipped with the LSM 510 confocal system (Zeiss, Jena, Germany).

We examined whether the differential sensitivity of breast cancer cell lines to the growth inhibitory effects of sulfamoylated estrones was related to differences in extent/phase of cell cycle arrest and/or cell death. These studies focused on 2-EtEMATE since we were readily able to synthesise relatively large amounts of this compound. We first examined the effects of 2-EtEMATE on the DNA content of MCF7, ZR-75-1, CAL51 and CAMA1 cells using flow cytometry of propidium iodide (PI) stained cells (FIG. 13 and Table 2). Cells were treated with 2-EtEMATE at 500 nM since this was the lowest dose that gave significant growth inhibition in each cell line (FIG. 14). MCF7 cells accumulated in the G2/M phase of the cell cycle within 24 hours and cells were maximally arrested (approximately 60% of cells) after 48 hours. This arrest was maintained for the duration of the experiment although there was a modest increase in cells with <G1 DNA content indicative of cell death at 72 and 96 hours. Similar results were obtained in ZR-75-1 cells although G2/M arrest was delayed in these cells (60% cells in G2/M after 72 hours). By contrast, CAL51 and CAMA1 cells which were more sensitive than MCF7 or ZR-75-1 cells in the microtitre plate assay (FIG. 14) underwent a more rapid G2/M arrest (approximately 60% of cells were in G2/M within 24 hours). In addition, 2-EtEMATE induced significant cell death within 48 hours and approximately half of the cells were dead after 96 hours (Table 2).

TABLE 2

Effect of 2-EtEMATE on DNA content of breast cancer cell lines. Cell cycle parameters of MCF7, ZR-75-1, CAL51 and CAMA1 cells exposed to 2-EtEMATE (500 nM) for up to 96 hours. The proportion of cells in G1/S or G2/M are shown as a percentage of total cells with a 2N to 4N DNA content. The proportion of cells with a sub-G1 DNA content is shown as percent of total cells. Untreated cells are at 96 hours.

| | Cell Line | | | | | |
|---|---|---|---|---|---|---|
| | MCF7 | | | ZR-75-1 | | |
| | <G1 | G1/S | G2/M | <G1 | G1/S | G2/M |
| Untreated | 2 | 77 | 23 | 1 | 79 | 20 |
| 24 hours | 5 | 63 | 37 | 1 | 84 | 15 |
| 48 hours | 5 | 38 | 62 | 6 | 60 | 40 |
| 72 hours | 12 | 34 | 66 | 12 | 37 | 63 |
| 96 hours | 8 | 29 | 71 | 9 | 20 | 80 |

| | Cell Line | | | | | |
|---|---|---|---|---|---|---|
| | CAL51 | | | CAMA1 | | |
| | <G1 | G1/S | G2/M | <G1 | G1/S | G2/M |
| Untreated | 1 | 78 | 22 | 4 | 70 | 30 |
| 24 hours | 2 | 38 | 62 | 4 | 33 | 67 |
| 48 hours | 10 | 18 | 82 | 16 | 25 | 75 |
| 72 hours | 21 | 32 | 68 | 36 | 33 | 67 |
| 96 hours | 44 | 23 | 77 | 51 | 33 | 67 |

Flow cytometric analysis demonstrated that cells treated with the sulfamoylated estrone deriviatives were arrested in G2/M phases of the cell cycle. Cells treated with 2-EtEMATE or 2-MeOEMATE often had a characteristic "rounded-up" morphology (Ref. 20 and data not shown) suggesting that cells were in fact arrested in mitosis. To determine whether cells were in interphase or mitosis, we stained drug-treated MCF7 cells with PI to visualise chromosomes. In preliminary experiments, we found that the "rounded up" cells did not fix to the collagen-treated glass slides that we used for fluorescence staining experiments and we therefore collected all of the cells by trypsinisation and prepared cytospins prior to staining. The vast majority of control MCF7 cells had a uniformly stained nucleus characteristic of interphase cells with uncondensed chromosomes (FIG. 15 and Table 3). By contrast, a significant proportion of cells treated with 2-EtEMATE or 2-MeOEMATE showed condensed chromosomes characteristic of mitosis. Therefore, the sulfamoylated estrone derivatives induce a mitotic arrest. Consistent with lack of effect in FACs assay (FIG. 13), the non-sulfamoylated estrone derivatives did not increase the number of mitotic cells. Since it was necessary to use cytospins in these experiments, it was difficult to determine the architecture of the chromosomes in cells treated with sulfamoylated estrone derivatives. However, the chromosomes appeared to be fully condensed suggesting that cells had reached pro-metaphase/metaphase.

Table 3. Effect of estrone derivatives on mitosis in MCF7 cells. MCF7 cells were treated with the indicated compounds for 24 hours. Cells were recovered by trypsinisation and cytospins prepared. DNA was stained with PI and cells in mitosis (i.e., with condensed chromosomes) determined as a percentage of total cells.

| Drug | mitotic cells |
| --- | --- |
| Control | 4% |
| 2-EtEMATE, 5 µM | 49% |
| 2-EtEMATE, 500 nM | 29% |
| 2-MeOEMATE, 5 µM | 38% |
| 2-MeOEMATE, 500 nM | 26% |
| 2-EtE1, 5 µM | 6% |
| 2-EtE1, 500 nM | 4% |

We used the TUNEL assay to confirm that the cell death detected by flow cytometry of PI stained cells was due to apoptosis. Following exposure to 2-EtEMATE (500 nM for 72 hours) there was a significant increase in the proportion of CAL51 and CAMA1 cells undergoing apoptosis (60% and 37% TUNEL positive cells, respectively) (FIG. 16). By contrast, there was only a modest increase in TUNEL positivity in MCF7 or ZR-75-1 cells (7% and 10%, respectively) treated with 2-EtEMATE at this concentration.

Taken together, these analyses demonstrate that the variations in the sensitivity of breast cancer cell lines to short term growth inhibition by sulfamoylated estrones are reflected in differences in effects on cell cycle and apoptosis. Although 2-EtEMATE induced a G2/M arrest in all cell lines, this was more rapid in relatively sensitive ER negative CAL51 and CAMA1 cells than in ER positive MCF7 and ZR-75-1 cells. Furthermore, 2-EtEMATE was a more potent inducer of apoptosis in CAL51 and CAMA1 cells than MCF7 and ZR-75-1 cells.

Discussion

Our results add further weight to the evidence showing that 2-methoxyoestrogens, or their synthetic analogues (23, 24), represent a new class of drugs for cancer therapy. The present compounds, such as 2-MeOEMATE, as previously found for 2-MeOE2, had a marked effect on the morphology and growth of MCF-7 and MDA-MD-231 breast cancer cells. Fibroblasts derived from breast tumours also showed a similar rounding in response to 2-MeOEMATE although a higher concentration was required to induce morphological changes in these cells.

The marked effect that 2-MeOEMATE has on the growth of ER+ and ER− breast cancer cells confirms that the present compounds such as 2-methoxyoestrogen sulphamates should be active against both hormone-dependent and independent breast tumours. At 1 µM 2-MeOE1 had little effect on the proliferation of MCF-7 cells while 2-MeOEMATE, at this concentration, inhibited proliferation by 52%. The reason for the increased potency conferred by the addition of a sulphamate group to 2-MeOE1 in the in vitro assays is not readily apparent. From in vivo studies with oestrogen sulphamates, it is known that these compounds are released slowly from rbcs to give a protracted increase in steroid blood concentration (17). Other in vivo studies have indicated that EMATE is capable of inactivating steroid sulphatase for a prolonged period of time after a single dose or multiple doses (25). Thus, it is likely that EMATE is binding to a cellular protein from which it is slowly released. This may account for the enhanced potency of the sulphamate in vitro compared with that of 2-MeOE1 in being able to reduce cell proliferation.

From the DNA analysis it is apparent that the present compounds, e.g. 2-MeOEMATE, like 2-MeOE2 and taxol, induce an arrest of cell cycling, in particular an arrest of cells in the $G_2/M$ phase of the cell cycle (9, 26, 27). For 2-MeOE2, however, a washout experiment, in which cells continued to be cultured in drug-free medium after an initial period of exposure to the drug, revealed that a significant proportion of cells re-entered the $G_1/S$ phase of the cell cycle by 24 h after removal of the drug (13). In contrast, for the compounds of the present invention (2-MeOEMATE) cells remained arrested in the $G_2/M$ phase for at least 24 h after removal of the drug. This finding provides further evidence that the present compounds may be binding to a cell protein.

2-MeOEMATE, while possessing novel anti-proliferative effects, remains a potent steroid sulphatase inhibitor (18).

Similar experiments in which MCF-7 cells were exposed to EMATE and then extensively washed to remove drug revealed that steroid sulphatase remained almost completely inactivated (28).

The ability of 2-MeOE2 to inhibit the growth of MCF-7 cells and to induce cells to become rounded and detached has previously been shown to result from its ability to induce apoptosis in these cells (8, 9). In the present investigation a significant increase in cells in the sub-$G_1$ fraction was detected after exposure to a present compound, namely 2-MeOEMATE. Cells in this fraction are thought to represent cells that have undergone apoptosis. TUNEL analysis confirmed that 2-MeOEMATE did induce a proportion of cells to undergo apoptosis. Like 2-MeOE2 and other drugs, such as taxol, that alter microtubule stability, the present compounds (2-MeOEMATE) probably induces apoptosis by increasing the phosphorylation of the oncoprotein Bcl-2 (27-29). Bcl-2 belongs to a family of proteins that are anti-apoptotic and their ability to inhibit apoptosis from their dimerisation with, and inactivation of proapototic proteins such as Bax (30, 31). Phosphorylation of Bcl-2 blocks its ability to dimerise with Bax thus allowing the induction of apoptosis. It has been clearly demonstrated that phosphorylation of Bcl-2 occurs during the arrest of cells in the $G_2/M$ phase of the cell cycle (30). In a preliminary study 2-MeOE2 was found to induce phosphorylation of Bcl-2 in leukaemia cells (29). This indicates that 2-methoxyoestrogens have a similar mechanism of action to that of taxol and other drugs that cause microtubule damage.

The marked effect that a present compound, especially 2-MeOEMATE, had on cell proliferation in vitro led to a preliminary in vivo study. In vivo an NMU-induced mammary tumour in one of the animals receiving 2-MeOE1 showed a modest (25%) regression. In contrast, ⅔ tumours in animals receiving 2-MeOEMATE regressed almost completely by the end of the 11-day study. The enhanced efficacy of 2-MeOEMATE compared with that of 2-MeOE1 lends support to the findings from the in vitro studies that the sulphamoylated estrogen is more potent than its parent compound.

Other in vivo tumour studies with the present compounds (2-methoxyoestrogens) have also produced encouraging results although at much higher than the doses employed in the present study. 2-MeOE2 (100 mg/kg, p.o.) when administered every other day to CH3 mice significantly reduced the growth of subcutaneously inoculated Meth A sarcoma and B16 melanoma tumours by 57% and 83% respectively (10). As in our study, this response was achieved in a relatively short, 12 day, period of time. In addition to inhibiting the growth of these tumours, tumour neovascularisation was markedly reduced. This suggests that an important action of 2-methoxyoestrogens in inhibiting tumour growth. Oral administration of 2-MeOE2 (75 mg/kg/day for 29 days) also suppressed the growth of tumours resulting from inoculation of the ER-MDA-MB-435 breast cancer cells in SCID mice (11). Tumour volumes were reduced by 60% compared with those of untreated controls. No toxic side effects were detected at this relatively high dosage of the drug. In addition to these animal studies, 2-MeOE2 is currently undergoing a Phase I/II trial although details of the outcome of this trial are not yet available (42, 43).

In the present in vivo studies, 2-MeOEMATE was employed although in vitro investigation has found that 2-MeOE2 is more potent than 2-MeOE1 (10). However, from experiments with estradiol sulphamate it is known that the 17-hydroxyl function is oxidised during gastric transit yet the reduced form of the steroid is released from rbcs (17). Therefore, there would appear to be no advantage to be gained from the oral administration of the reduced form of 2-MeOEMATE.

As most cancers eventually become resistant to either hormone or chemotherapy the development of drugs that act on different cellular targets offers considerable hope for the development of new cancer therapies. The therapeutic use of taxol has been an important advance but problems with its solubility and toxicity have limited its prolonged use. The identification of 2-MeOEMATE as a form of 2-methoxyoestrogen with enhanced efficacy, bioavailability and duration of action suggests that this drug should have considerable potential for cancer therapy.

Thus, in summary, the present invention provides a composition and compound suitable for use in the treatment of cancers and, especially, breast cancer.

In particular, in one aspect the present invention addresses the problem of blocking the growth of cancers including leukaemias and solid tumours such as breast, endometrium, prostate, ovary and pancreatic tumours.

It is also believed that the present invention has implications in treating hormonal conditions in addition to those associated with oestrogen. Hence, the present invention also provides a composition that is capable of affecting hormonal activity and is capable of affecting an immune response, wherein the composition is the composition of the present invention.

It is also to be understood that the compound/composition of the present invention may have other important medical implications.

For example, the composition of the present invention may be useful in the treatment of the disorders listed in WO-A-98/05635. For ease of reference, part of that list is now provided: cancer, inflammation or inflammatory disease, dermatological disorders, fever, cardiovascular effects, haemorrhage, coagulation and acute phase response, cachexia, anorexia, acute infection, HIV infection, shock states, graft-versus-host reactions, autoimmune disease, reperfusion injury, meningitis, migraine and aspirin-dependent anti-thrombosis; tumour growth, invasion and spread, angiogenesis, metastases, malignant, ascites and malignant pleural effusion; cerebral ischaemia, ischaemic heart disease, osteoarthritis, rheumatoid arthritis, osteoporosis, asthma, multiple sclerosis, neurodegeneration, Alzheimer's disease, atherosclerosis, stroke, vasculitis, Crohn's disease and ulcerative colitis; periodontitis, gingivitis; psoriasis, atopic dermatitis, chronic ulcers, epidermolysis bullosa; corneal ulceration, retinopathy and surgical wound healing; rhinitis, allergic conjunctivitis, eczema, anaphylaxis; restenosis, congestive heart failure, endometriosis, atherosclerosis or endosclerosis.

In addition, or in the alternative, the composition of the present invention may be useful in the treatment of disorders listed in WO-A-98/07859. For ease of reference, part of that list is now provided: cytokine and cell proliferation/differentiation activity; immunosuppressant or immunostimulant activity (e.g. for treating immune deficiency, including infection with human immune deficiency virus; regulation of lymphocyte growth; treating cancer and many autoimmune diseases, and to prevent transplant rejection or induce tumour immunity); regulation of haematopoiesis, e.g. treatment of myeloid or lymphoid diseases; promoting growth of bone, cartilage, tendon, ligament and nerve tissue, e.g. for healing wounds, treatment of burns, ulcers and periodontal disease and neurodegeneration; inhibition or activation of follicle-stimulating hormone (modulation of fertility); chemotactic/chemokinetic activity (e.g. for mobilising specific cell types to sites of injury or infection); haemostatic and thrombolytic activity (e.g. for treating haemophilia and stroke); antiinflammatory activity (for treating e.g. septic shock or Crohn's disease); as antimicrobials; modulators of e.g. metabolism or behaviour; as analgesics; treating specific deficiency disorders; in treatment of e.g. psoriasis, in human or veterinary medicine.

In addition, or in the alternative, the composition of the present invention may be useful in the treatment of disorders listed in WO-A-98/09985. For ease of reference, part of that list is now provided: macrophage inhibitory and/or T cell inhibitory activity and thus, anti-inflammatory activity; anti-immune activity, i.e. inhibitory effects against a cellular and/or humoral immune response, including a response not associated with inflammation; inhibit the ability of macrophages and T cells to adhere to extracellular matrix components and fibronectin, as well as up-regulated fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g. retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chora, myasthenia gravis, pseudo-tumour cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue.

Protocol I

Irreversible Inhibition

Procedure
Stage 1
MCF-7 breast cancer cells were seeded into multi-well culture plates at a density of $10^5$ cells/well. Cells were allowed to attach and grown until about 30% confluent when they were treated as follows:
  Control—no treatment
  Compound of Interest (COI) 20 μM
Cells were grown for 6 days in growth medium containing the COI with changes of medium/COI every 3 days. At the end of this period cell numbers were counted using a Coulter cell counter.
State 2
After treatment of cells for a 6-day period with the COI cells were re-seeded at a density of $10^4$ cells/well. No further treatments were added. Cells were allowed to continue to grow for a further 6 days in the presence of growth medium. At the end of this period cell numbers were again counted.

All publications and patents mentioned in the above specification are herein incorporated by reference.

Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

REFERENCES

1. Nebert, D. W. Proposed role of drug-metabolising enzymes: regulation of steady-state levels of the ligands that effect growth, homeostasis, differentiation and neuroendocrine function. Molec. Endocrinol., 5: 1203-1214, 1991.
2. Reed, M. J., Purohit, A., Woo, L. W. L., and Potter, B. V. L. The development of steroid sulphatase inhibitors. Endocr.-Rel. Cancer, 3: 9-23, 1996.
3. Bradlow, H. L., Michnovicz, J. J., Telang, N. T., and Osborne, M. P. Effect of dietary indole-3-carbinol on oestradiol metabolism and spontaneous tumours in mice. Carcinogenesis, 12: 1571-1574, 1991.
4. Bradlow, H. L., Sepkovic, D. W., Telang, N. T., and Osborne, M. P. Indole-3-carbinol: a novel approach to breast cancer prevention. Ann. N.Y. Acad. Sci., 728: 180-200, 1995.
5. Bradlow, H. L., Davis, D. L., Lin, G., Sepkovic, D. W., and Tiwari, R. Effects of pesticides on the ratio of 16α/2-hydroxyoestrone: a biological marker of breast cancer risk. Environ. Health Perspect., 103 (Suppl.): 147-150, 1995.
6. Bradlow, H. L., Telang, N. T., Sepkovic, D. W., and Osborne, M. P. 2-Hydroxyoestrone: the 'good' estrogen. J. Endocrinol., 150: S259-S265, 1996.
7. Zhu, B. T., and Conney, A. H. Is 2-methoxyoestradiol an endogenous estrogen metabolite that inhibits mammary carcinogenesis. Cancer Res., 58: 2269-2277, 1998.
8. Seegers, J. C., Aveling, M.-L., Van Aswegen, C. H., Cross, M., Koch, F., and Joubert, W. S. The cytotoxic effects of oestradiol-17β, catecholoestradiols and methoxyoestradiols on dividing MCF-7 and HeLa cells. J. Steroid Biochem., 32: 797-809, 1989.
9. Seegers, J. C., Lottering, M. L., Grobler, C. J., Van Papendorp, D. H., Habbersett, R. C., Shou, Y., and Lehnert, B. E. The mammalian metabolite, 2-methoxyoestradiol affects p53 levels and apoptosis induction in transformed cells but not in normal cells. J. Steroid Biochem. Molec. Biol., 62: 253-267, 1997.
10. Fotsis, T., Zhang, Y., Pepper, M. S., Adlercreutz, H., Montesano, R., Nawroth, P. P., and Schweigerer, L. The endogenous oestrogen metabolite 2-methoxyoestradiol inhibits angiogenesis and suppresses tumour growth. Nature, 368: 237-239, 1994.
11. Klauber, N., Parangi, S., Flynn, E., Hamel, E., and D'Amato, R. J. Inhibition of angiogenesis and breast cancer in mice by the microtubule inhibitors 2-methoxyoestradiol and taxol. Cancer Res., 57: 81-86, 1997.
12. D'Amato, R. J., Lin, C. M., Flynn, E., Folkman, J., and Hamel, E. 2-Methoxyestradiol, an endogenous mammalian metabolite, inhibits tubulin polymerization by interacting at the colchicine site. Proc. Natl. Acad. Sci. USA, 91: 3964-3968, 1994. AND U.S. Pat. No. 5,504,074
13. Attalla, H., Mäkelä, T. P., Adlercreutz, H., and Andersson, L. C. 2-Methoxyoestradiol arrests cells in mitosis without depolymerising tubulin. Biochem. Biophys. Res. Comm., 228: 467-473, 1996.
14. Howarth, N. M., Purohit, A., Reed, M. J., and Potter, B. V. L. Estrone sulphamates: potent inhibitors of oestrone sulphatase with therapeutic potential. J. Med. Chem., 37: 219-221, 1994.

15. Purohit, A., Williams, G. J., Howarth, N. M., Potter, B. V. L., and Reed, M. J. Inactivation of steroid sulphatase by an active site-directed inhibitor, oestrone-3-O-sulphamate. Biochemistry, 34: 11508-11514, 1995.
16. Elger, W., Schwarz, S., Hedden, A., Reddersen, G., and Schneider, B. Sulphamates of various oestrogens as prodrugs with increased systemic and reduced hepatic oestrogenicity at oral application. J. Steroid Biochem. Molec, Biol., 55: 395-403, 1995.
17. Elger, W., Palme, H.-J., and Schwarz, S. Novel oestrogen sulphamates: a new approach to oral hormone therapy. Exp. Opin. Invest. Drugs, 7: 575-589, 1998.
18. Purohit, A., Vernon, K. A., Wagenaar-Humelinck, A. E., Woo, L. W. L., Hejaz, H. A. M., Potter, B. V. L., and Reed, M. J. The development of A-ring modified analogues of oestrone-3-O-sulphamate as steroid sulphatase inhibitors with reduced oestrogenicity. J. Steroid Biochem. Molec. Biol., 64: 269-275, 1998.
19. Purohit, A., Hejaz., H. A. M., Woo, L. W. L., Van Strien, A. E., Potter, B. V. L., and Reed, M. J. Recent advances in the development of steroid sulphatase inhibitors. J. Steroid Biochem. Molec. Biol. (In Press).
20. Woo, L. W. L., Purohit, A., Reed, M. J., and Potter, B. V. L. Active site directed inhibition of oestrone sulphatase by non-steroidal coumarin sulphamates. J. Med. Chem., 39: 1349-1351, 1996.
21. Wilkinson, J. R., Williams, J. C., Singh, D., Goss, P. E., Easton, D., and Coombes, R. C. Response of nitrosomethylurea-induced rat mammary tumor to endocrine therapy and comparison with clinical response. Cancer Res., 46: 4862-4865, 1986.
22. Vera, J. C., Reyes, A. M., Carcamo, J. G., Velasquez, F. V., Rivas, C. I., Zhang, R. H., Strobel, P., Iribarren, R., Scher, H. I., Slebe, J. C., and Golde, D. W. Genistein is a natural inhibitor of hexose and dehydroascorbic acid transport through the glucose transporter, GLUT 1. J. Biol. Chem., 271: 8719-8724, 1996.
23. Cushman, M., H e, H.-M., Katzenellenbogen, J. A., Lin, C. M., and Hamel, E. Synthesis, antitubulin and antimitotic activity and cytotoxicity of analogues of 2-methoxyoestradiol, an endogenous mammalian metabolite of oestradiol that inhibits tubulin polymerisation by binding to the colchicine binding site. J. Med. Chem., 38: 2041-2049, 1995.
24. Cushman, M., H e, H.-M., Katzenellenbogen, J. A., Varma, R. K., Hamel, E., Lin, C. M., Ram, S., and Sachdeva, Y. P. Synthesis of analogues of 2-methoxyoestradiol with enhanced inhibitory effects on tubulin polymerisation and cancer cell growth. J. Med. Chem., 40: 2323-2334, 1997.
25. Purohit, A., Williams, G. J., Roberts, C. J., Potter, B. V. L., and Reed, M. J. In vivo inhibition of oestrone sulphatase and dehydroepiandrosterone sulphatase by oestrone-3-O-sulphamate. Int. J. Cancer, 63: 106-111, 1995.
26. Haldar, S., Jena, N., and Croce, C. M. Inactivation of bcl-2 by phosphorylation. Proc. Natl. Acad. Sci. USA, 92: 4507-4511, 1995.
27. Haldar, S., Chintapalli, J., and Croce, C. M. Taxol induces bcl-2 phosphorylation and death of prostate cancer cells. Cancer Res., 56: 1253-1255, 1996.
28. Purohit, A., Reed, M. J., Morris, N. C., Williams, G. J., and Potter, B. V. L. Regulation and inhibition of steroid sulphatase activity in breast cancer. Ann. N.Y. Acad. Sci., 784: 40-49, 1996.
29. Attalla, H., Westberg, J. A., Andersson, L. C., Adlercreutz, H., and Makela, T. P. 2-Methoxyestradiol-induced phosphorylation of Bcl-2: uncoupling from JNK/SAPK activation. Biochem. Biophys. Res. Comm., 247: 616-619, 1998.
30. Haldar, S., Basu, A., and Croce, C. M. Bcl-2 is the guardian of microtubule integrity. Cancer Res., 57: 229-233, 1997.
31. Blagosklonny, M. V., Giannakakou, P., El-Deiry, W. S., Kingston, D. G. T., Higgs, P. I., Neckers, L., and Fojo, T. Raf-1/bcl-2 phosphorylation: a step from microtubule damage to cell death. Cancer Res., 57: 130-135, 1997.
32. Constantinou, A. I., Kamath, N., and Murley, J. S. Genistein inactivates bcl-2, delays the $G_2/M$ phase of the cell cycle and induces apoptosis of human breast adenocarcinoma MCF-7 cells. Eur. J. Cancer, 34: 1927-1934, 1998.
33. Akiyama, T., Ishida, J., Nakagawa, S., Ogawara, H., Watanabe, S.-I., Itoh, N., Shibuya, M., and Fukami, Y. Genistein, a specific inhibitor of tyrosine-specific protein kinases. J. Biol. Chem., 262: 5592-5595, 1987.
34. Flier, J. S., Mueckler, M. M., Usher, P., and Lodish, H. F. Elevated levels of glucose transport and transporter messenger RNA are induced by ras or src oncogenes. Science, 235: 1492-1495, 1987.
35. Shim, H., Chun, Y.-S., Lewis, B. C., and Dang, C. V. A unique glucose-dependent apoptotic pathway induced by c-myc. Proc. Natl. Acad. Sci. USA, 95: 1511-1516, 1998.
36. Gould, G. W., and Holman, G. D. The glucose transporter family: structure, function and tissue-specific expression. Biochem. J., 295: 329-341, 1993.
37. Brown, R. S., and Wahl, R. L. Overexpression of GLUT-1 glucose transporter in human breast cancer. Cancer, 72: 2979-2985, 1993.
38. Younes, M., Lechago, L. V., Somoano, J. R., Mosharaf, M., and Lechago, J. Wide expression of the human erythrocyte glucose transporter GLUT-1 in human cancers. Cancer Res., 56: 1164-1167, 1996.
39. Zamora-Leon, P., Golde, D. W., Concha, I. I., Rivas, C. I., Delgado-Lopez, F., Baselga, J., Nualart, F., and Vera, J. C. Expression of the fructose transporter GLUT-5 in human breast cancer. Proc. Natl. Acad. Sci., 93: 1847-1852, 1996.
40. Tsakiridis, T., Vranic, M., and Klip, A. Disassembly of the actin network inhibits insulin-dependent stimulation of glucose transport and prevents recruitment of glucose transporters to the plasma membrane. J. Biol. Chem., 269: 29934-29942, 1994.
41. Hamilton-Wessler, M., Ader, M., Getty, L., Dea, M., Hamm-Alvarez, S., and Bergman, R. N. Microtubule-disrupting agent taxol reduces insulin-stimulated glucose uptake in vivo. Diabetes, 45 (Suppl. 2): Abstr. 615, 1996.
42. Brem, S. Angiogenesis antagonists: current clinical trials. Angiogenesis, 2: 9-20, 1998.
43. Harris, A. L. Are angiostatin and endostatin cures for cancer? Lancet, 351: 1598-1599, 1998.
44. Appel R and Berger G. Über das Hydrazidosulphamide (on hydrazidosulphamide) *Chemische Berichte* 1958; 91; 1339.
45. Perrin D D and Amarego W L F. Purification of laboratory chemicals. *Pergamon press*; Oxford 1988; 290.

The invention claimed is:

1. A method of treating a cancer, in a subject in need thereof, wherein said cancer is estrogen independent and wherein said cancer is susceptible to being treated by inhibition or arresting of cell cycling, by a cyclic compound or pharmaceutically active salt thereof, said method comprising inhibiting or arresting cell cycling by the cyclic compound or pharmaceutically active salt thereof by administering to said subject, the cyclic compound or a pharmaceutically active salt thereof in an amount sufficient to inhibit or arrest cell cycling and thus treat the cancer susceptible to being treated by inhibition or arresting of cell cycling by the cyclic compound or pharmaceutically active salt thereof, wherein the cyclic compound comprises a polycyclic ring structure to which is attached a Group I and a Group II, independently of each other, wherein the polycyclic ring structure has the formula:

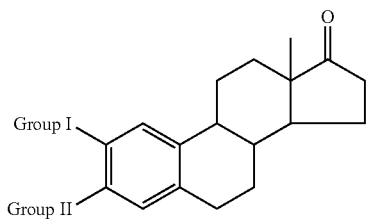

wherein Group I is an alkoxy or alkyl; and wherein Group II is an unsubstituted sulphamate.

2. The method of claim 1 wherein the cyclic compound or pharmaceutically active salt thereof irreversibly inhibits and/or arrests cell cycling.

3. The method of claim 1 wherein cell cycling is inhibited and/or arrested in the $G_2/M$ phase.

4. The method of claim 1 wherein the alkoxy is a methoxy group.

5. The method of claim 1 wherein the alkyl is an ethyl group.

6. The method of claim 1 wherein the cyclic compound or pharmaceutically active salt thereof is administered with a pharmaceutically acceptable carrier, diluent or excipient.

7. The method of claim 1 wherein the cancer is breast cancer, ovarian cancer, endometrial cancer, a sarcoma, a melanoma, prostate cancer, or pancreatic cancer.

8. The method of claim 1 wherein the cancer is a solid tumor.

9. The method of claim 1 wherein the cancer is breast cancer.

10. The method of claim 1 wherein the cyclic compound is non-oestrogenic.

11. A method of treating a cancer, in a subject in need thereof, wherein said cancer is estrogen independent and wherein said cancer is susceptible to being treated by inhibition or arresting of cell cycling, by a cyclic compound or pharmaceutically active salt thereof, said method comprising inhibiting or arresting cell cycling by the cyclic compound or pharmaceutically active salt thereof by administering to said subject, the cyclic compound or a pharmaceutically active salt thereof in an amount sufficient to inhibit or arrest cell cycling and thus treat the cancer susceptible to being treated by inhibition or arresting of cell cycling by the cyclic compound or pharmaceutically active salt thereof, wherein the cyclic compound is 2-methoxyoestrone-3-O-sulphamate or 2-ethyloestrone-3-O-sulphamate.

12. The method of claim 11 wherein the cyclic compound is 2-methoxyoestrone-3-O-sulphamate.

13. The method of claim 11 wherein the cyclic compound is 2-ethyloestrone-3-O-sulphamate.

14. The method of claim 11 wherein the cancer is breast cancer, ovarian cancer, endometrial cancer, a sarcoma, a melanoma, prostate cancer, or pancreatic cancer.

15. The method of claim 11 wherein the cancer is a solid tumor.

16. The method of claim 11 wherein the cancer is breast cancer.

17. The method of claim 11 wherein the cyclic compound is non-oestrogenic.

* * * * *